(12) United States Patent
Joshi

(10) Patent No.: US 8,129,585 B2
(45) Date of Patent: Mar. 6, 2012

(54) METHODS FOR ENHANCING EXPRESSION OF SECONDARY CELL WALL CELLULOSE SYNTHASES IN PLANTS

(75) Inventor: Chandrashekhar P. Joshi, Houghton, MI (US)

(73) Assignee: Michigan Technological University, Houghton, MI (US)

( * ) Notice: Subject to any disclaimer, the term of this patent is extended or adjusted under 35 U.S.C. 154(b) by 743 days.

(21) Appl. No.: 11/997,503

(22) PCT Filed: Aug. 3, 2006

(86) PCT No.: PCT/US2006/030316
§ 371 (c)(1),
(2), (4) Date: May 19, 2008

(87) PCT Pub. No.: WO2007/019245
PCT Pub. Date: Feb. 15, 2007

(65) Prior Publication Data
US 2008/0222752 A1 Sep. 11, 2008

Related U.S. Application Data

(60) Provisional application No. 60/705,033, filed on Aug. 3, 2005.

(51) Int. Cl.
*C12N 15/82* (2006.01)
*C12N 15/63* (2006.01)
*C12N 15/09* (2006.01)
*A01H 5/00* (2006.01)

(52) U.S. Cl. ............... 800/278; 800/295; 435/320.1; 435/468; 536/23.1; 536/23.6

(58) Field of Classification Search .......... None
See application file for complete search history.

(56) References Cited

U.S. PATENT DOCUMENTS

| | | | |
|---|---|---|---|
| 5,268,274 A | 12/1993 | Ben-Bassat et al. | |
| 5,633,439 A | 5/1997 | Walter et al. | |
| 5,646,023 A | 7/1997 | Secor et al. | |
| 5,654,190 A | 8/1997 | Matsunaga et al. | |
| 6,013,860 A | 1/2000 | Himmel et al. | |
| 6,271,443 B1 * | 8/2001 | Stalker et al. | 800/298 |
| 6,303,847 B1 | 10/2001 | Kawaoka et al. | |
| 6,867,352 B2 | 3/2005 | Allen | |
| 7,049,481 B1 | 5/2006 | Chiang et al. | |
| 7,232,941 B2 | 6/2007 | Chiang et al. | |
| 7,288,409 B1 | 10/2007 | Chiang et al. | |
| 2002/0120124 A1 * | 8/2002 | Allen | 536/23.6 |
| 2005/0108791 A1 | 5/2005 | Edgerton | |

FOREIGN PATENT DOCUMENTS

| | | |
|---|---|---|
| CA | 2012311 | 9/1990 |
| EP | 875575 | 11/1998 |
| WO | WO 98/00549 | 1/1998 |
| WO | WO 98/18949 | 5/1998 |
| WO | WO 00/22092 | 4/2000 |
| WO | WO 00/71670 | 11/2000 |

OTHER PUBLICATIONS

Chandrashekhar 2003 Applied Biochemistry and Biotechnology 105:17-25, provided by Applicant.*
Accession No. T10797—Sequence Search Result (1996) 1-2.
Alt-Morbe, et al., "Differences in induction of Ti plasmid virulence genes virG and virD, and continued control of virD expression by four external factors," Mol. Plant.-Microbe. Interact. (1989) 2(6):301-308.
Arioli, T.L. et al., "Molecular analysis of cellulose biosynthesis in Arabidopsis," Science (1998) 279:717-720.
Benton, W.D. et al., "Screening λgt recombinant clones by hybridization to single plaques in situ," Science (1977) 196:180-182.
Bird et al., "Manipulation of Plant Gene expression by Antisense RNA," *Biotechnology & Genetic Engineering Reviews* (1991) 9:207-227.
Brown, R.M. et al., "Cellulose biosynthesis in higher plants," Trends Plant Sci. (1996) 1(5):149-156.
Bugos, R.C. et al., "RNA isolation from plant tissues recalcitrant to extraction in guanidine," Biotechniques (1995) 19:734-737.
Delmer, D.P. et al., "Cellulose biosynthesis," The Plant Cell (1995) 7:987-1000.
Djerbi, S. et al., "Identification and expression analysis of genes encoding putative cellulose synthases (CesA) in the hybrid aspen, Populus tremula (L.) x P. tremuloides (Michx.)," Cellulose (2004) 11:301-312.
Esau, K., Anatomy of Seed Plants, New York: John Wiley and Sons. (1960).
Esau, K., Plant Anatomy, $2^{nd}$ ed. New York: Wiley (1953).
Esau, K., Vascular Differentiation in Plants, New York: Hold, Rinehart & Winston (1965).
Esau, K., et al., "Observations on Cytokinesis", *Planta* (Berl.) 67, 168-181 (1965).
Esau, K., "Anatomy of Plant Virus Infections", *Annu. Rev. Phytopathol.* 5:45-76 (1967).
Freshney, R.I., "Immobilised Cells and Enzymes", Animal Cell Culture: A Practical Approach. 1986. IRL Press. Fukuda, H., "Xylogenesis: initiation, progression, and cell death," Ann. Rev. Plant Physiol. Plant Mol. Biol. (1996) 47:299-325.
Fullner, K.J. et al., "Temperature affects the T-DNA transfer machinery of agrobacterium tumefaciens," J. Bacteriol. (1996) 178(6):1498-1504.
Fullner, K.J. et al., "Pilus assembly by agrobacterium T-DNA transfer genes," Science (1996) 273:1107-1109.
Ge, L. et al., A full-length cDNA encoding trans-cinnamate 4-hydroxylase from developing xylem of populus tremuloides (Accession No. U47293) Plant Physiol. (1996) 112:861-864.
Grunstein, M. et al., "Colony hybridization: a method for the isolation of cloned DNAs that contain a specific gene," Proc. Natl. Acad. Sci. (1975) 72(10):3961-3965.
Haigler, C. et al., "New hopes for old dreams: evidence that plant cellulose synthase genes have finally been cloned," Porc. Natl. Acad. Sci., 93: 12082-12085, (1996).

(Continued)

Primary Examiner — Brent T Page
(74) Attorney, Agent, or Firm — Michael Best & Friedrich LLP

(57) ABSTRACT

Described are methods for making transgenic plants capable of expressing secondary cell wall cellulose synthases and methods of enhancing expression of secondary cell wall cellulose synthases in plants. Also described are plants produced by the methods. Plants comprising at least three exogenous polynucleotides encoding secondary cell wall cellulose synthases are also provided.

17 Claims, 8 Drawing Sheets

OTHER PUBLICATIONS

Higuchi, R. "Using PCR to Engineer DNA", in *PCR Technology: Principles and Applications for DNA Amplification*, H. Erlich, ed., Stockton Press, Chapter 6, pp. 61-70. (1989).

Higuchi, R., Biochemistry and Molecular Biology of Wood, Springer Verlag (1997).

Hofmann, K. et al., "A database of membrane spanning protein segments," MF C-35, Biol. Chem. Hoppe-Seyler (1993) 374:166.

Hu, W-J. et al., "Repression of lignin biosynthesis promotes cellulose accumulation and growth in transgenic trees," Nature Biotech. (1999) 17:808-812.

Hu, W-J. et al., "Compartmentalized expression of two structurally and functionally distinct 4-coumarate: CoA ligase genes in aspen (Populus tremuloides)," Proc. Natl. Acad. Sci. USA (1998) 95:5407-5412.

Hutchinson, C.A., et al., "Mutagenesis at a Specific Position in a DNA Sequence", *J. Biol. Chem.*, 253:6551 (1978).

Hutchinson, C.A. et al., "A complete library of point substitution mutations in the glucocorticoid response element of mouse mammary tumor virus," *Proc. Natl. Acad. Sci. U.S.A.* (1986) 83:710-714.

Joshi, C.P. et al., "Context sequences of translation initiation codon in plants," Plant Mol. Biol. (1997) 35:993-1001.

Joshi, C.P. et al., "An inspection of the domain between purative TA TA box and translation start site in 79 plant genes," Nuc. Acids Res. (1987) 15(16):6643-6653.

Joshi, C.P. et al., "Putative polyadenylation signals in nuclear genes of higher plants: a compilation and analysis," Nuc. Acids Res. (1987) 15:9627-9640.

Joshi, C.P. et al., "Genomics of cellulose biosynthesis in poplars," New Phytologist (2004) 164:53-61.

Joshi, J.P. et al., "Xylem-specific and tension stress-responsive expression of cellulose synthase genes from aspen trees," Appl. Biochem. Biotech. (2003) 105-108:17-25.

Joshi, J.P., "Molecular biology of cellulose biosynthesis in plants," Recent Res. Devel. Plant Mol. Biol. (2003) 1:19-38.

Kalluri, U.C. et al., "Differential expression patterns of two cellulose synthase genes are associated with primary and secondary cell wall development in aspen trees," Planta. (2004) 220:47-55.

Kalluri, U.C. et al., "Isolation and characterization of a new, full-length cellulose synthase cDNA, PtrCesA5 from developing xylem of aspen trees," J. Exp. Botany (2003) 54(390):2187-2188.

Lazar et al., "Transforming Growth Factor α: Mutation of Aspartic Acid 47 and Leucine 48 Results in Different Biological Activities," *Molec. & Cell. Biol.* (1988) 8(3):1247-1252.

Li, L. et al., "Combinatorial modification of multiple lignin traits in trees through multigene cotransformation," Proc. Natl. Acad. Sci. USA (2003) 100:4939-4944.

Liang, X. et al., "Molecular cloning of ten distinct hypervariable regions from the cellulose synthase gene superfamily in aspen trees," Tree Physiology (2004) 24:543-550.

Lu, S-F, et al., Molecular cloning and characterization of three cellulose synthases assciated with xylem development in *Eucalyptus grandis*, Poster presented at American Society of Plant Biologists annual meeting at Denver, CO, Aug. 2-7, 2002.

Matton, D.P., et al., "Identification of cis-acting elements involved in the Regulation of the Pathogenesis-related Gene STH-2 in Potato" *Plant Molecular Biology*, 102:279-291, (1993).

Nakai, T. et al., Control of expression by the cellulose synthase (bcsA) promoter region from Acetrobacter xylinum BPR 2002 *Gene*, 213(1-2):93-100, (1998).

Needleman, S.B. et al., "A general method applicable to the search for similarities in the amino acid sequence of two proteins," *J. Mol. Biol* (1970) 48:443-453.

Oliphant, A.R. et al., "Cloning of random-sequence oligodeoxynucleotides," Gene (1986) 44:177-183.

Pear, J.R. et al., "Higher Plants Contain Homologs of the Bacterial celA Genes Encoding The Catalytic Subunit of Cellulose Synthase"*Proc. Natl. Acad. Sci*, 93:12637-12642, (1996).

Salvucci, M.E. et al., "Identification of the Uridine-Binding Domain of Sucrose-Phosphate Synthase" *Plant Physiology*, 102:529-536, (1993).

Samuga, A. et al., Accession No. AY095297, "A new cellulose synthase gene (PtrCesA2) from Aspen xylem is orthologous to Arabidopsis AtCesA7 (irx3) gene associated with secondary cell wall synthesis," Gene (2002) 296(1-2):37-44.

Saxena, I.M. et al., "Cloning and Sequenceing of the Cellulose Synthase Catalytic Subunit Gene of the Acetobactre Xylinum" *Plant Molecular Biology*, 15:673-683, (1990).

Smith, C.J.S. et al., "Antisense RNA Inhibition of Polygalacturonase Gene Expression in Transfenic Tomatoes," *Nature* (1988) 334:724-726.

Song, Y-R. et al., "Tissue-print hybridization on membrane for localization of mRNA in plant tissue," Methods in Enzymology (1993) 218:671-681.

Tsai, C.J. et al., "Agrobacterium-mediated transformation of quaking aspen (populus tremuloides) and regeneration of transgenic plants," Plant Cell Reports (1994) 14:94-97.

Tsai, C.J. et al., "Suppression of O-methyltransferase gene by homologous sense transgene in quaking aspen causes red-brown wood phenotypes," Plant Physiology (1998) 117(5):101-112.

Whetten, R.W. et al., "Recent advances in understanding lignin biosynthesis," Ann. Rev. Pl. Physiol. Pl. Mol. Biol. (1998) 49:585-609.

Wilson, J.M. et al., "Hepatocyte-directed gene transfer in vivo leads to transient improvement of hypercholesterolemia in low density lipoprotein receptor-deficient rabbits," J. Biol. Chem. (1992) 267:963-967.

Wu, G.Y. et al., "Receptor-mediated gene delivery and expression in vivo," *J. Biol. Chem.* (1988) 263:14621-14624.

Wu, L. et al., "AraxCelA, a new member of the cellulose synthase gene family from Arabidopsis (Accession No. AF062485)," Plant Physiol. (1998) 117:1125.

Wu, L. et al., Accession No. AF072131, "A xylem-specific cellulose synthase gene from Aspen (Populus tremuloides) is responsive to mechanical stress," Plant J. (2000) 22(6):495-502.

Wu, L. et al., "A xylem-specific cellulose synthase gene from aspen (populus tremuloides) is responsive to mechanical stress," EBI Database Accession No. 081368 (1998).

Ye, Z-H. et al., "Gene expression patterns associated with in vitro tracheary element formation in isolated single mesophyll cells of zinnia elegans," Plant Physiol. (1993) 103(3):805-813.

Zhou, Y., et al., "Molecular cloning of cellulose synthase genes from loblolly pine", Poster presented at American Society of Plant Biologists annual meeting at Denver, CO, Aug. 2-7, 2002.

Zoller, M.J. et al., "Oligonucleotide-directed mutagenesis: a simple method using two oligonucleotide primers and a single-stranded DNA template," DNA (1984) 3(6):479-488.

International Search Report and Written Opinion for Application No. PCT/US2006/030316 dated Jul. 16, 2007 (11 pages).

* cited by examiner

```
Secondary cell wall cellulose synthases related to PtrCesA1

Plurality: 8.00   Threshold: 3   AveWeight 1.00   AveMatch 2.78   AvMisMatch -2.25
                          1                                             50
SEQ ID NO:8    AF323039{Ze1}      YGPQSLPTLP SPSSSS...S CCCCGPKKPK KDLEEFKRDA RRDDLNAAIF
SEQ ID NO:9    AF323040{Ze2}      YGPQSLPTLP SPSSSS...S CCCCGPKKEK KDLEEFKRDA RRDDLNAAIF
SEQ ID NO:10   AF323041{Ze3}      YGPQSLPTLP SPSSSS...S CCCCGPKKPK KDLEEFKRDA RRDDLNAAIF
SEQ ID NO:11   GHU58283{Gh1}      YGPPSMPSFP SPSSSS.C.S CCCPGKKEP. KDPSELYRDA KREELDAAIF
SEQ ID NO:12   AF413210{Gh4}      YGPPSMPSFP KSSSSS.C.S CCCPGKKEP. KEPTELYRDA KREELDAAIF
SEQ ID NO:13   AC125473{Mt3}      YSPPSMPPLP K..SSS.C.. CCFPSKKPA. KDVSELYKDA KREELDAAIF
SEQ ID NO:14   AP003237{Os4}      YGPPSLPALP KSSVCSWC.C CCCPKKKAE. KSEKEMHRDS RREDLESAIF
SEQ ID NO:15   AF072131{P1}       YGPPSMPSLR KRKDSSSCFS CCCPSKKKPA QDPAEVYRDA KREDLNAAIF
SEQ ID NO:16   AF267742{A8}       YSPPSKPRIL PQSSSS...S CCCLTKKKQP QDPSEIYKDA KREELDAAIF
               Consensus          Y-P-S-P---  ----SS----  CCC----K---  ----E----DA  -R--L-AAIF 51                                            100
SEQ ID NO:8    AF323039{Ze1}      NLKEIESYDD YERSLLISQM SFEKTFGMSS VFIESTLMEN GGLAESANPA
SEQ ID NO:9    AF323040{Ze2}      NLKEIESYDD YERSLLISQM SFEKTFGMSS VFIESTLMEN GGLAESANPA
SEQ ID NO:10   AF323041{Ze3}      NLKEIESYDD YERSLLISQM SFEKTFGMSS VFIESTLMEN GGLAESANPA
SEQ ID NO:11   GHU58283{Gh1}      NLREIDNYDE YERSMLISQT SFEKTFGLSS VFIESTLMEN GGVAESANPS
SEQ ID NO:12   AF413210{Gh4}      NLREIDNYDE YERSMLISQT SFEKTFGLSS VFIESTLMEN GGVAESANPS
SEQ ID NO:13   AC125473{Mt3}      NLREIENYDE YERSMLISQL SFEKTFGLST VFIESTLMEN GGVSESADPS
SEQ ID NO:14   AP003237{Os4}      NLREIDNYDE YERSMLISQM SFEKSFGLSS VFIESTLMEN GGVPESANPS
SEQ ID NO:15   AF072131{P1}       NLTEIDNYDE HERSMLISQL SFEKTFGLSS VFIESTLMEN GGVPESANSP
SEQ ID NO:16   AF267742{A8}       NLGDIDNYDE YDRSMLISQT SFEKTFGLST VFIESTLMEN GGVPDSVNPS
               Consensus          NL-EI--YD- YERS-LISQ- SFEKTFG-S-I VFIESTLMEN GG--ESANP- 101
SEQ ID NO:8    AF323039{Ze1}      TMINEAIH
SEQ ID NO:9    AF323040{Ze2}      TMINEAIH
SEQ ID NO:10   AF323041{Ze3}      TMINEAIH
SEQ ID NO:11   GHU58283{Gh1}      TLIKEAIH
SEQ ID NO:12   AF413210{Gh4}      TLIKEAIH
SEQ ID NO:13   AC125473{Mt3}      MLIKEAIH
SEQ ID NO:14   AP003237{Os4}      TLIKEAIH
SEQ ID NO:15   AF072131{P1}       TLIKEAIH
SEQ ID NO:16   AF267742{A8}       TLIKEAIH
               Consensus          T-I-EAIH
```

FIG. 2A

```
Secondary cell wall cellulose synthases related to PtrCesA2

Plurality: 4.00   Threshold: 3   AveWeight 1.00   AveMatch 2.78   AvMisMatch -2.25

1                                                        50
SEQ ID NO:17  AP004509{Lj2}   YNPPKGPKRP KMVSCDCCPC FGSRKK.LKH AKSDVNGEAA SLKGMDD.DK
SEQ ID NO:18  AC140546{Mt8}   YNPPKGPKRP KMVSCDCCPC FGRKKK.VKH AMNDANGEAA GLRGMED.DK
SEQ ID NO:19  AF088917{A7}    YEPPKGPKRP KMISCGCCPC FGRRRKNKKE SKNDMNGDVA ALGGAEG.DK
SEQ ID NO:20  AY095297{P2}    YDPPKDPKRP KMETCDCCPC EGRRKK.... .KNAKTG..A VVEGMDNNDK
SEQ ID NO:21  AP004509{Lj1}   FDPPKASKR. .......... ...QREVQVH SKQDESGEDG SIKEATDEDK
              Consensus       Y-PPK-PKRP KM--C-CCPC FG-R-K---- -K-D--G--A ----G----DK 51                                                       95
SEQ ID NO:17  AP004509{Lj2}   EVLMSQMNFE KKFGQSSIFV TSTLMEEGGV PPSSSPAGML KEAIH
SEQ ID NO:18  AC140546{Mt8}   ELLMSQMNFE KKFGQSSIFV TSVLMEEGGV PPSSSPASQL KEAIH
SEQ ID NO:19  AF088917{A7}    EHLMFEMNFE KTFGQSSIFV TSTLMEEGGV PPSSSPAVLL KEAIH
SEQ ID NO:20  AY095297{P2}    ELLMSHMNFE KKFGQSAIFV TSTLMEEGGV PPSSSPAALL KEAIH
SEQ ID NO:21  AP004509{Lj1}   QLLKSHMNVE NKFGNSTLFM NSSLTEEGGV DPSSSQEALL KEAIH
              Consensus       E-LMS-MNFE KKFGQS-IFV TS-LMEEGGV PPSSSPA---L KEAIH
```

FIG. 2B

```
Secondary cell wall cellulose synthases related to PtrCesA3

Plurality:  5.00    Threshold:  3    AveWeight  1.00    AveMatch  2.78    AvMisMatch  -2.25

1                                                              50
SEQ ID NO:22  AF527387 (P3)    YDPPVSEKRP KMTCDCWPSW CCCCF...GG SRKKS.KKK.  GQ.RSLLGG.
SEQ ID NO:23  AF081534 (Pc)    YDPPVSEKRP KMTCDCWPSW CCCCF...GG SRKKS.KKK.  GQ.RSLLGG.
SEQ ID NO:24  GHU58284 (Gh2)   YDPPVSEKRP KMTCDCWPSW CCCCC...GG SRKKS.KKK.  GEKKGLLGGL
SEQ ID NO:25  AC131248 (Mt2)   YDPPVSEKRP KMTCDCWPKW CCFCC...GS RKTKS.KKKS  CTNGRSLFSR
SEQ ID NO:26  AF458083 (A4)    YEPPVSEKRK KMTCDCWPSW ICCCC...GG GNRNH.KSDS  SKKKSGIKSL
SEQ ID NO:27  AC022457 (Os7)   YDPPRPEKRP KMTCDCWP3W CCCCCCTGGG KRGKSHKNKK  GGGGEGGGL
              Consensus        YDPPVSEKRP KMTCDCWPSW CCCC------GG ---KS-K-K-  G--------

51                                                             100
SEQ ID NO:22  AF527387 (P3)    ..........L YPMKKKRMMGK ........KYT RKA.SA..PV  FDLEEIEEGL
SEQ ID NO:23  AF081534 (Pc)    ..........L YPMKKKRMMGK ........KYT RKA.SA..PV  FDLEEIEEGL
SEQ ID NO:24  GHU58284 (Gh2)   ..........L YGKKKKRMMGK ........NYV KKG.SA..PV  FDLEEIEEGL
SEQ ID NO:25  AC131248 (Mt2)   ..........L Y.KKKKMGGK .........DYV RKG.SG..SM  FDLEEIEQGL
SEQ ID NO:26  AF458083 (A4)    ..........F SKLKKTKKK SDDKTMSSYS RKR.SSTEAI  FDLEDIEEGL
SEQ ID NO:27  AC022457 (Os7)   DEPRRGLLGF YKKRSKKDKL GGGAASLAGG KKGYRKHQRG  FELEEIEEGL
              Consensus        ---------Y- --KKK----K -----------Y- --K--S---  FDLEEIEEGL 101                                                            150
SEQ ID NO:22  AF527387 (P3)    EGYEELEKSS LMSQKSFEKR FGQSPVFIAS TLMENGGVPE  G...TNSQSHI
SEQ ID NO:23  AF081534 (Pc)    EGYEELEKSS LMSQKSLEKR FGQSPVFIAS TLMENGGVPE  G...TNSQSHI
SEQ ID NO:24  GHU58284 (Gh2)   EGYEELEKST LMSQKNFEKR FGQSPVFIAS TLMENGGLPE  G...TNSTSLI
SEQ ID NO:25  AC131248 (Mt2)   EGYDELEKSS LMSQKSFEKR FGQSPVFIAS TLMENGGLPE  G...TNTQSLV
SEQ ID NO:26  AF458083 (A4)    EGYEELEKSS LMSQKSFEKR FGMSPVFIAS TLMENGGLPE  A..TNTSSLI
SEQ ID NO:27  AC022457 (Os7)   EGYDELERSS LMSQKSFEKR FGQSPVFIAS TLVEDGGLPQ  GAAADPAALI
              Consensus        EGY-ELEKSS LMSQK-FEKR FGQSPVFIAS TLMENGG-PE  G--TN-S-I 151
SEQ ID NO:22  AF527387 (P3)    KEAIH
SEQ ID NO:23  AF081534 (Pc)    KEAIH
SEQ ID NO:24  GHU58284 (Gh2)   KEAIH
SEQ ID NO:25  AC131248 (Mt2)   KEAIH
SEQ ID NO:26  AF458083 (A4)    KEAIH
SEQ ID NO:27  AC022457 (Os7)   KEAIH
              Consensus        
```

FIG. 2C

Phylogenetic tree of CesA Cellulose Synthase members

PtrCesA1/pBI121
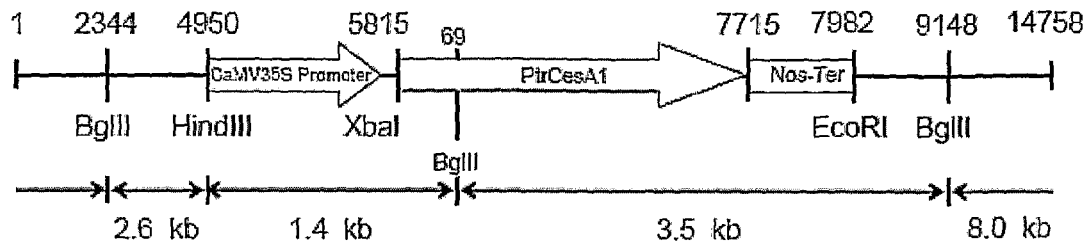
PtrCesA2/pBI121
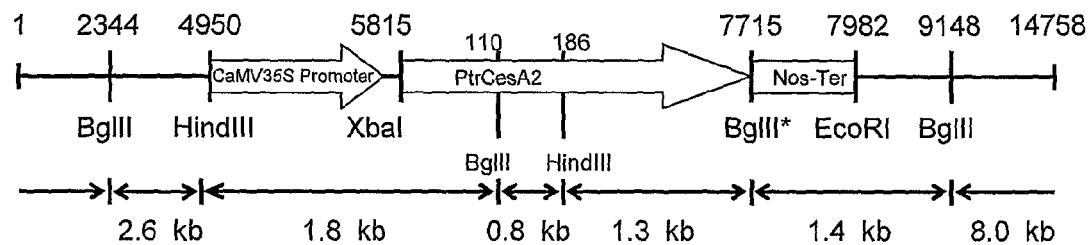
PtrCesA3/pBI121
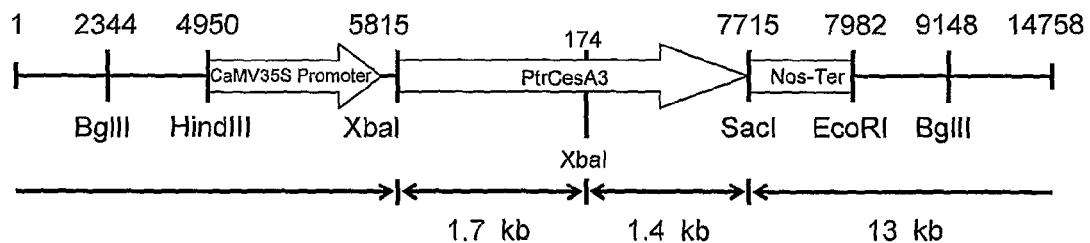
* This BglII site was created via ligation.
FIG. 4B

A        B        C
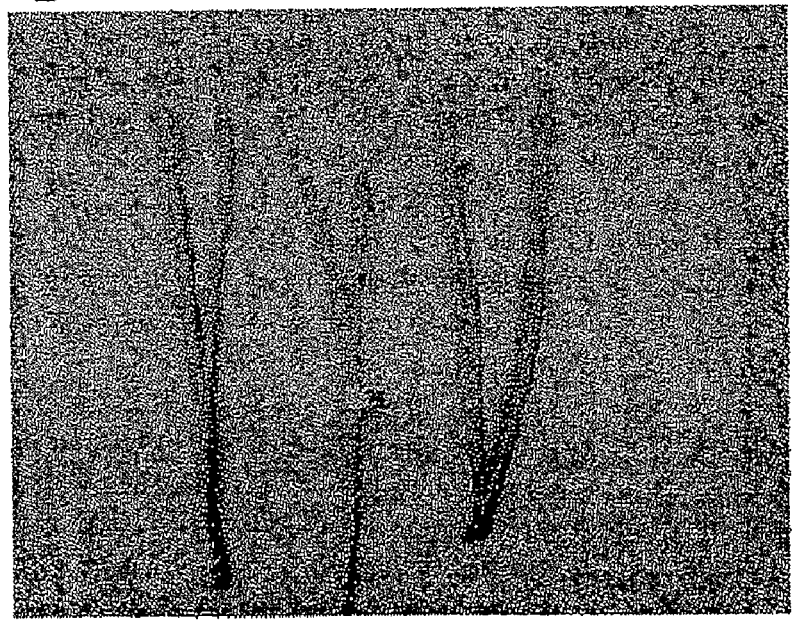
FIG. 5

SEQUENCE LISTING

```
<160> NUMBER OF SEQ ID NOS: 27

<210> SEQ ID NO 1
<211> LENGTH: 3232
<212> TYPE: DNA
<213> ORGANISM: Populus tremuloides
<220> FEATURE:
<221> NAME/KEY: CDS
<222> LOCATION: (69)..(3005)

<400> SEQUENCE: 1
gtcgacccac gcgtccgtct tgaaagaata tgaagttgta aagagctggt aaagtggtaa      60 taagcaag atg atg gaa tct ggg gct cct ata tgc cat acc tgt ggt gaa     110
         Met Met Glu Ser Gly Ala Pro Ile Cys His Thr Cys Gly Glu
         1               5                   10 cag gtg ggg cat gat gca aat ggg gag cta ttt gtg gct tgc cat gag     158
Gln Val Gly His Asp Ala Asn Gly Glu Leu Phe Val Ala Cys His Glu
15                  20                  25                  30 tgt agc tat ccc atg tgc aag tct tgt ttc gag ttt gaa atc aat gag     206
Cys Ser Tyr Pro Met Cys Lys Ser Cys Phe Glu Phe Glu Ile Asn Glu
                35                  40                  45 ggc cgg aaa gtt tgc ttg cgg tgt ggc tcg cca tat gat gag aac ttg     254
Gly Arg Lys Val Cys Leu Arg Cys Gly Ser Pro Tyr Asp Glu Asn Leu
            50                  55                  60 ctg gat gat gta gaa aag aag ggg tct ggc aat caa tcc aca atg gca     302
Leu Asp Asp Val Glu Lys Lys Gly Ser Gly Asn Gln Ser Thr Met Ala
        65                  70                  75 tct cac ctc aac gat tct cag gat gtc gga atc cat gct aga cat atc     350
Ser His Leu Asn Asp Ser Gln Asp Val Gly Ile His Ala Arg His Ile
    80                  85                  90 agt agt gtg tcc act gtg gat agt gaa atg aat gat gaa tat ggg aat     398
Ser Ser Val Ser Thr Val Asp Ser Glu Met Asn Asp Glu Tyr Gly Asn
95                  100                 105                 110 cca att tgg aag aat cgg gtg aag agc tgt aag gat aaa gag aac aag     446
Pro Ile Trp Lys Asn Arg Val Lys Ser Cys Lys Asp Lys Glu Asn Lys
                115                 120                 125 aag aaa aag aga agt cct aag gct gaa act gaa cca gct caa gtt cct     494
Lys Lys Lys Arg Ser Pro Lys Ala Glu Thr Glu Pro Ala Gln Val Pro
            130                 135                 140 aca gaa cag cag atg gaa gag aaa ccg tct gca gag gct tcg gag ccg     542
Thr Glu Gln Gln Met Glu Glu Lys Pro Ser Ala Glu Ala Ser Glu Pro
        145                 150                 155 ctt tca att gtt tat cca att cca cgc aac aag ctc aca cca tac aga     590
Leu Ser Ile Val Tyr Pro Ile Pro Arg Asn Lys Leu Thr Pro Tyr Arg
    160                 165                 170 gca gtg atc att atg cga ctg gtc att ctg ggc ctc ttc ttc cac ttc     638
```

-continued

| | | |
|---|---|---|
| Ala Val Ile Ile Met Arg Leu Val Ile Leu Gly Leu Phe Phe His Phe<br>175                    180                    185                    190 | | |
| aga ata aca aat cct gtc gat agt gcc ttt ggc ctg tgg ctt act tct<br>Arg Ile Thr Asn Pro Val Asp Ser Ala Phe Gly Leu Trp Leu Thr Ser<br>                195                    200                    205 | 686 | |
| gtc ata tgt gag atc tgg ttt gca ttt tct tgg gtg ttg gat cag ttc<br>Val Ile Cys Glu Ile Trp Phe Ala Phe Ser Trp Val Leu Asp Gln Phe<br>            210                    215                    220 | 734 | |
| ccc aag tgg aat cct gtc aat aga gaa acg tat atc gaa agg ctg tcg<br>Pro Lys Trp Asn Pro Val Asn Arg Glu Thr Tyr Ile Glu Arg Leu Ser<br>      225                    230                    235 | 782 | |
| gca agg tat gaa aga gag ggt gag cct tct cag ctt gct ggt gtg gat<br>Ala Arg Tyr Glu Arg Glu Gly Glu Pro Ser Gln Leu Ala Gly Val Asp<br>240                    245                    250 | 830 | |
| ttt ttc gtg agt act gtt gat ccg ctg aag gaa ccg cca ttg atc act<br>Phe Phe Val Ser Thr Val Asp Pro Leu Lys Glu Pro Pro Leu Ile Thr<br>255                    260                    265                    270 | 878 | |
| gcc aat aca gtc ctt tcc atc ctt gct gtg gac tat ccc gtc gat aaa<br>Ala Asn Thr Val Leu Ser Ile Leu Ala Val Asp Tyr Pro Val Asp Lys<br>                275                    280                    285 | 926 | |
| gtc tcc tgc tac gtg tct gat gat ggt gca gct atg ctt tca ttt gaa<br>Val Ser Cys Tyr Val Ser Asp Asp Gly Ala Ala Met Leu Ser Phe Glu<br>            290                    295                    300 | 974 | |
| tct ctt gta gaa aca gct gag ttt gca agg aag tgg gtt ccg ttc tgc<br>Ser Leu Val Glu Thr Ala Glu Phe Ala Arg Lys Trp Val Pro Phe Cys<br>      305                    310                    315 | 1022 | |
| aaa aaa ttc tca att gaa cca aga gca ccg gag ttt tac ttc tca cag<br>Lys Lys Phe Ser Ile Glu Pro Arg Ala Pro Glu Phe Tyr Phe Ser Gln<br>320                    325                    330 | 1070 | |
| aaa att gat tac ttg aaa gac aag gtt caa cct tct ttc gtg aaa gaa<br>Lys Ile Asp Tyr Leu Lys Asp Lys Val Gln Pro Ser Phe Val Lys Glu<br>335                    340                    345                    350 | 1118 | |
| cgt aga gca atg aaa agg gat tat gaa gag tac aaa gtc cga gtt aat<br>Arg Arg Ala Met Lys Arg Asp Tyr Glu Glu Tyr Lys Val Arg Val Asn<br>                355                    360                    365 | 1166 | |
| gcc ctg gta gca aag gct cag aaa aca cct gaa gaa gga tgg act atg<br>Ala Leu Val Ala Lys Ala Gln Lys Thr Pro Glu Glu Gly Trp Thr Met<br>            370                    375                    380 | 1214 | |
| caa gat gga aca cct tgg cct ggg aat aac aca cgt gat cac cct ggg<br>Gln Asp Gly Thr Pro Trp Pro Gly Asn Asn Thr Arg Asp His Pro Gly<br>      385                    390                    395 | 1262 | |
| cat gat tca ggt ctt cct tgg gaa ata ctg gga gct cgt gac att gaa<br>His Asp Ser Gly Leu Pro Trp Glu Ile Leu Gly Ala Arg Asp Ile Glu<br>400                    405                    410 | 1310 | |
| gga aat gaa cta cct cgt cta gta tat gtc tcc agg gag aag aga cct<br>Gly Asn Glu Leu Pro Arg Leu Val Tyr Val Ser Arg Glu Lys Arg Pro<br>415                    420                    425                    430 | 1358 | |
| ggc tac cag cac cac aaa aag gct ggt gca gaa aat gct ctg gtg aga<br>Gly Tyr Gln His His Lys Lys Ala Gly Ala Glu Asn Ala Leu Val Arg<br>                435                    440                    445 | 1406 | |
| gtg tct gca gta ctc aca aat gct ccc tac atc ctc aat gtt gat tgt<br>Val Ser Ala Val Leu Thr Asn Ala Pro Tyr Ile Leu Asn Val Asp Cys<br>            450                    455                    460 | 1454 | |
| gat cac tat gta aac aat agc aag gct gtt cga gag gca atg tgc atc<br>Asp His Tyr Val Asn Asn Ser Lys Ala Val Arg Glu Ala Met Cys Ile<br>      465                    470                    475 | 1502 | |
| ctg atg gac cca caa gta ggt cga gat gta tgc tat gtg cag ttc cct<br>Leu Met Asp Pro Gln Val Gly Arg Asp Val Cys Tyr Val Gln Phe Pro<br>480                    485                    490 | 1550 | |
| cag agg ttt gat ggc ata gat aag agt gat cgc tac gcc aat cgt aac | 1598 | |

-continued

| | | | | | | | | | | | | | | | |
|---|---|---|---|---|---|---|---|---|---|---|---|---|---|---|---|
| Gln | Arg | Phe | Asp | Gly | Ile | Asp | Lys | Ser | Asp | Arg | Tyr | Ala | Asn | Arg | Asn |
| 495 | | | | | 500 | | | | | 505 | | | | | 510 |

```
gta gtt ttc ttt gat gtt aac atg aaa ggg ttg gat ggc att caa gga    1646
Val Val Phe Phe Asp Val Asn Met Lys Gly Leu Asp Gly Ile Gln Gly
                        515                 520                 525 cca gta tac gta gga act ggt tgt gtt ttc aac agg caa gca ctt tac    1694
Pro Val Tyr Val Gly Thr Gly Cys Val Phe Asn Arg Gln Ala Leu Tyr
                    530                 535                 540 ggc tac ggg cct cct tct atg ccc agc tta cgc aag aga aag gat tct    1742
Gly Tyr Gly Pro Pro Ser Met Pro Ser Leu Arg Lys Arg Lys Asp Ser
                545                 550                 555 tca tcc tgc ttc tca tgt tgc tgc ccc tca aag aag aag cct gct caa    1790
Ser Ser Cys Phe Ser Cys Cys Cys Pro Ser Lys Lys Lys Pro Ala Gln
            560                 565                 570 gat cca gct gag gta tac aga gat gca aaa aga gag gat ctc aat gct    1838
Asp Pro Ala Glu Val Tyr Arg Asp Ala Lys Arg Glu Asp Leu Asn Ala
575                 580                 585                 590 gcc ata ttt aat ctt aca gag att gat aat tat gac gag cat gaa agg    1886
Ala Ile Phe Asn Leu Thr Glu Ile Asp Asn Tyr Asp Glu His Glu Arg
                595                 600                 605 tca atg ctg atc tcc cag ttg agc ttt gag aaa act ttt ggc tta tct    1934
Ser Met Leu Ile Ser Gln Leu Ser Phe Glu Lys Thr Phe Gly Leu Ser
            610                 615                 620 tct gtc ttc att gag tct aca cta atg gag aat gga gga gta ccc gag    1982
Ser Val Phe Ile Glu Ser Thr Leu Met Glu Asn Gly Gly Val Pro Glu
        625                 630                 635 tct gcc aac tca cca cca ttc atc aag gaa gcg att caa gtc atc ggc    2030
Ser Ala Asn Ser Pro Pro Phe Ile Lys Glu Ala Ile Gln Val Ile Gly
    640                 645                 650 tgt ggc tat gaa gag aag act gaa tgg gga aaa cag att ggt tgg ata    2078
Cys Gly Tyr Glu Glu Lys Thr Glu Trp Gly Lys Gln Ile Gly Trp Ile
655                 660                 665                 670 tat ggg tca gtc act gag gat atc tta agt ggc ttc aag atg cac tgc    2126
Tyr Gly Ser Val Thr Glu Asp Ile Leu Ser Gly Phe Lys Met His Cys
                675                 680                 685 cga gga tgg aga tca att tac tgc atg ccc gta agg cct gca ttc aaa    2174
Arg Gly Trp Arg Ser Ile Tyr Cys Met Pro Val Arg Pro Ala Phe Lys
            690                 695                 700 gga tct gca ccc atc aac ctg tct gat aga ttg cac cag gtc ctc cga    2222
Gly Ser Ala Pro Ile Asn Leu Ser Asp Arg Leu His Gln Val Leu Arg
        705                 710                 715 tgg gct ctt ggt tct gtg gaa att ttc ttt agc aga cac tgt ccc ctc    2270
Trp Ala Leu Gly Ser Val Glu Ile Phe Phe Ser Arg His Cys Pro Leu
    720                 725                 730 tgg tac ggg ttt gga gga ggc cgt ctt aaa tgg ctc caa agg ctt gcg    2318
Trp Tyr Gly Phe Gly Gly Gly Arg Leu Lys Trp Leu Gln Arg Leu Ala
735                 740                 745                 750 tat ata aac acc att gtg tac cca ttt aca tcc ctc cct ctc att gcc    2366
Tyr Ile Asn Thr Ile Val Tyr Pro Phe Thr Ser Leu Pro Leu Ile Ala
                755                 760                 765 tat tgc aca att cct gca gtt tgt ctg ctc acc gga aaa ttc atc ata    2414
Tyr Cys Thr Ile Pro Ala Val Cys Leu Leu Thr Gly Lys Phe Ile Ile
            770                 775                 780 cca acg ctc tca aac ctg gca agc atg ctg ttt ctt ggc ctc ttt atc    2462
Pro Thr Leu Ser Asn Leu Ala Ser Met Leu Phe Leu Gly Leu Phe Ile
        785                 790                 795 tcc atc att gta act gcg gtg ctt gag cta aga tgg agc ggt gtc agc    2510
Ser Ile Ile Val Thr Ala Val Leu Glu Leu Arg Trp Ser Gly Val Ser
    800                 805                 810 att gaa gat tta tgg cgt aat gaa caa ttc tgg gtg atc gga ggt gtt    2558
```

```
Ile Glu Asp Leu Trp Arg Asn Glu Gln Phe Trp Val Ile Gly Gly Val
815                 820                 825                 830 tca gcc cat ctc ttt gcg gtc ttc cag gga ttc tta aaa atg ttg gct    2606
Ser Ala His Leu Phe Ala Val Phe Gln Gly Phe Leu Lys Met Leu Ala
                    835                 840                 845 ggc atc gat acg aac ttc act gtc aca gca aaa gca gcc gaa gat gca    2654
Gly Ile Asp Thr Asn Phe Thr Val Thr Ala Lys Ala Ala Glu Asp Ala
            850                 855                 860 gaa ttt ggg gag cta tat atg gtc aag tgg aca aca ctt tgg att cct    2702
Glu Phe Gly Glu Leu Tyr Met Val Lys Trp Thr Thr Leu Trp Ile Pro
        865                 870                 875 cca acc aca ctt ctc att atc aat atg tcg ggt tgt gct gga ttc tct    2750
Pro Thr Thr Leu Leu Ile Ile Asn Met Ser Gly Cys Ala Gly Phe Ser
    880                 885                 890 gat gca ctc aac aaa gga tat gaa gca tgg ggg cct ctc ttt ggc aag    2798
Asp Ala Leu Asn Lys Gly Tyr Glu Ala Trp Gly Pro Leu Phe Gly Lys
895                 900                 905                 910 gtg ttc ttt gct ttc tgg gtg att ctt cat ctc tat cca ttc ctt aaa    2846
Val Phe Phe Ala Phe Trp Val Ile Leu His Leu Tyr Pro Phe Leu Lys
                    915                 920                 925 ggt cta atg ggt cgc caa aac cta aca cca acc att gtt gtt ctc tgg    2894
Gly Leu Met Gly Arg Gln Asn Leu Thr Pro Thr Ile Val Val Leu Trp
            930                 935                 940 tca gtg ctg ttg gcc tct gtc ttc tct ctc gtt tgg gtc aag atc aat    2942
Ser Val Leu Leu Ala Ser Val Phe Ser Leu Val Trp Val Lys Ile Asn
        945                 950                 955 cca ttc gtt aac aaa gtt gat aac acc ttg gtt gcg gag acc tgc att    2990
Pro Phe Val Asn Lys Val Asp Asn Thr Leu Val Ala Glu Thr Cys Ile
    960                 965                 970 tcc att gat tgc tga gctacctcca ataagtctct cccagtattt tggggttaca    3045
Ser Ile Asp Cys
975 aaacctttgg gaattggaat atgatcctcg ttgtagtttc cctcaagaaa gcacatatcg    3105 ctgtcagtat ttaaatgaac tgcaagatga ttgttctcta tgaagttttg aacagtttga    3165 aatgatatta tgttaaaata caggttttga ttgtgttgaa aaaaaaaaag aaaaaaaaaa    3225 aaaaaaa                                                              3232

<210> SEQ ID NO 2
<211> LENGTH: 978
<212> TYPE: PRT
<213> ORGANISM: Populus tremuloides

<400> SEQUENCE: 2

Met Met Glu Ser Gly Ala Pro Ile Cys His Thr Cys Gly Glu Gln Val
1               5                   10                  15

Gly His Asp Ala Asn Gly Glu Leu Phe Val Ala Cys His Glu Cys Ser
            20                  25                  30

Tyr Pro Met Cys Lys Ser Cys Phe Glu Phe Glu Ile Asn Glu Gly Arg
        35                  40                  45

Lys Val Cys Leu Arg Cys Gly Ser Pro Tyr Asp Glu Asn Leu Leu Asp
    50                  55                  60

Asp Val Glu Lys Lys Gly Ser Gly Asn Gln Ser Thr Met Ala Ser His
65                  70                  75                  80

Leu Asn Asp Ser Gln Asp Val Gly Ile His Ala Arg His Ile Ser Ser
                85                  90                  95

Val Ser Thr Val Asp Ser Glu Met Asn Asp Glu Tyr Gly Asn Pro Ile
            100                 105                 110
```

```
Trp Lys Asn Arg Val Lys Ser Cys Lys Asp Lys Glu Asn Lys Lys Lys
            115                 120                 125

Lys Arg Ser Pro Lys Ala Glu Thr Glu Pro Ala Gln Val Pro Thr Glu
130                 135                 140

Gln Gln Met Glu Glu Lys Pro Ser Ala Glu Ala Ser Glu Pro Leu Ser
145                 150                 155                 160

Ile Val Tyr Pro Ile Pro Arg Asn Lys Leu Thr Pro Tyr Arg Ala Val
                165                 170                 175

Ile Ile Met Arg Leu Val Ile Leu Gly Leu Phe Phe His Phe Arg Ile
            180                 185                 190

Thr Asn Pro Val Asp Ser Ala Phe Gly Leu Trp Leu Thr Ser Val Ile
        195                 200                 205

Cys Glu Ile Trp Phe Ala Phe Ser Trp Val Leu Asp Gln Phe Pro Lys
    210                 215                 220

Trp Asn Pro Val Asn Arg Glu Thr Tyr Ile Glu Arg Leu Ser Ala Arg
225                 230                 235                 240

Tyr Glu Arg Glu Gly Glu Pro Ser Gln Leu Ala Gly Val Asp Phe Phe
                245                 250                 255

Val Ser Thr Val Asp Pro Leu Lys Glu Pro Pro Leu Ile Thr Ala Asn
            260                 265                 270

Thr Val Leu Ser Ile Leu Ala Val Asp Tyr Pro Val Asp Lys Val Ser
        275                 280                 285

Cys Tyr Val Ser Asp Asp Gly Ala Ala Met Leu Ser Phe Glu Ser Leu
    290                 295                 300

Val Glu Thr Ala Glu Phe Ala Arg Lys Trp Val Pro Phe Cys Lys Lys
305                 310                 315                 320

Phe Ser Ile Glu Pro Arg Ala Pro Glu Phe Tyr Phe Ser Gln Lys Ile
                325                 330                 335

Asp Tyr Leu Lys Asp Lys Val Gln Pro Ser Phe Val Lys Glu Arg Arg
            340                 345                 350

Ala Met Lys Arg Asp Tyr Glu Glu Tyr Lys Val Arg Val Asn Ala Leu
        355                 360                 365

Val Ala Lys Ala Gln Lys Thr Pro Glu Glu Gly Trp Thr Met Gln Asp
    370                 375                 380

Gly Thr Pro Trp Pro Gly Asn Asn Thr Arg Asp His Pro Gly His Asp
385                 390                 395                 400

Ser Gly Leu Pro Trp Glu Ile Leu Gly Ala Arg Asp Ile Glu Gly Asn
                405                 410                 415

Glu Leu Pro Arg Leu Val Tyr Val Ser Arg Glu Lys Arg Pro Gly Tyr
            420                 425                 430

Gln His His Lys Lys Ala Gly Ala Glu Asn Ala Leu Val Arg Val Ser
        435                 440                 445

Ala Val Leu Thr Asn Ala Pro Tyr Ile Leu Asn Val Asp Cys Asp His
    450                 455                 460

Tyr Val Asn Asn Ser Lys Ala Val Arg Glu Ala Met Cys Ile Leu Met
465                 470                 475                 480

Asp Pro Gln Val Gly Arg Asp Val Cys Tyr Val Gln Phe Pro Gln Arg
                485                 490                 495

Phe Asp Gly Ile Asp Lys Ser Asp Arg Tyr Ala Asn Arg Asn Val Val
            500                 505                 510

Phe Phe Asp Val Asn Met Lys Gly Leu Asp Gly Ile Gln Gly Pro Val
        515                 520                 525

Tyr Val Gly Thr Gly Cys Val Phe Asn Arg Gln Ala Leu Tyr Gly Tyr
530                 535                 540
```

```
Gly Pro Pro Ser Met Pro Ser Leu Arg Lys Arg Lys Asp Ser Ser
545                 550                 555                 560

Cys Phe Ser Cys Cys Cys Pro Ser Lys Lys Lys Pro Ala Gln Asp Pro
                565                 570                 575

Ala Glu Val Tyr Arg Asp Ala Lys Arg Glu Asp Leu Asn Ala Ala Ile
            580                 585                 590

Phe Asn Leu Thr Glu Ile Asp Asn Tyr Asp Glu His Glu Arg Ser Met
            595                 600                 605

Leu Ile Ser Gln Leu Ser Phe Glu Lys Thr Phe Gly Leu Ser Ser Val
    610                 615                 620

Phe Ile Glu Ser Thr Leu Met Glu Asn Gly Gly Val Pro Glu Ser Ala
625                 630                 635                 640

Asn Ser Pro Pro Phe Ile Lys Glu Ala Ile Gln Val Ile Gly Cys Gly
                645                 650                 655

Tyr Glu Glu Lys Thr Glu Trp Gly Lys Gln Ile Gly Trp Ile Tyr Gly
                660                 665                 670

Ser Val Thr Glu Asp Ile Leu Ser Gly Phe Lys Met His Cys Arg Gly
            675                 680                 685

Trp Arg Ser Ile Tyr Cys Met Pro Val Arg Pro Ala Phe Lys Gly Ser
    690                 695                 700

Ala Pro Ile Asn Leu Ser Asp Arg Leu His Gln Val Leu Arg Trp Ala
705                 710                 715                 720

Leu Gly Ser Val Glu Ile Phe Phe Ser Arg His Cys Pro Leu Trp Tyr
                725                 730                 735

Gly Phe Gly Gly Gly Arg Leu Lys Trp Leu Gln Arg Leu Ala Tyr Ile
                740                 745                 750

Asn Thr Ile Val Tyr Pro Phe Thr Ser Leu Pro Leu Ile Ala Tyr Cys
            755                 760                 765

Thr Ile Pro Ala Val Cys Leu Leu Thr Gly Lys Phe Ile Ile Pro Thr
    770                 775                 780

Leu Ser Asn Leu Ala Ser Met Leu Phe Leu Gly Leu Phe Ile Ser Ile
785                 790                 795                 800

Ile Val Thr Ala Val Leu Glu Leu Arg Trp Ser Gly Val Ser Ile Glu
                805                 810                 815

Asp Leu Trp Arg Asn Glu Gln Phe Trp Val Ile Gly Gly Val Ser Ala
            820                 825                 830

His Leu Phe Ala Val Phe Gln Gly Phe Leu Lys Met Leu Ala Gly Ile
            835                 840                 845

Asp Thr Asn Phe Thr Val Thr Ala Lys Ala Ala Glu Asp Ala Glu Phe
    850                 855                 860

Gly Glu Leu Tyr Met Val Lys Trp Thr Thr Leu Leu Ile Pro Pro Thr
865                 870                 875                 880

Thr Leu Leu Ile Ile Asn Met Ser Gly Cys Ala Gly Phe Ser Asp Ala
                885                 890                 895

Leu Asn Lys Gly Tyr Glu Ala Trp Gly Pro Leu Phe Gly Lys Val Phe
            900                 905                 910

Phe Ala Phe Trp Val Ile Leu His Leu Tyr Pro Phe Leu Lys Gly Leu
            915                 920                 925

Met Gly Arg Gln Asn Leu Thr Pro Thr Ile Val Val Leu Trp Ser Val
    930                 935                 940

Leu Leu Ala Ser Val Phe Ser Leu Val Trp Val Lys Ile Asn Pro Phe
945                 950                 955                 960

Val Asn Lys Val Asp Asn Thr Leu Val Ala Glu Thr Cys Ile Ser Ile
```

Asp Cys

<210> SEQ ID NO 3
<211> LENGTH: 3277
<212> TYPE: DNA
<213> ORGANISM: Populus tremuloides
<220> FEATURE:
<221> NAME/KEY: CDS
<222> LOCATION: (21)..(3119)

<400> SEQUENCE: 3

| | | | | | | | | | | | |
|---|---|---|---|---|---|---|---|---|---|---|---|
| ggcacgaggc attcttcagc | atg | gaa | gct | agt | gct | gga | ctg | gtc | gca | ggc tct | 53 |
| | Met | Glu | Ala | Ser | Ala | Gly | Leu | Val | Ala | Gly Ser | |
| | 1 | | | 5 | | | | | 10 | | |

| cac | aac | cgc | aac | gag | ctt | gtt | gtc | att | cat | ggc | cat | gaa | gag | cat | aaa | 101 |
|---|---|---|---|---|---|---|---|---|---|---|---|---|---|---|---|---|
| His | Asn | Arg | Asn | Glu | Leu | Val | Val | Ile | His | Gly | His | Glu | Glu | His | Lys | |
| | | 15 | | | | 20 | | | | | 25 | | | | | |

| cct | ttg | aag | aac | ttg | gat | ggt | caa | gtt | tgt | gag | att | tgt | ggc | gat | gag | 149 |
|---|---|---|---|---|---|---|---|---|---|---|---|---|---|---|---|---|
| Pro | Leu | Lys | Asn | Leu | Asp | Gly | Gln | Val | Cys | Glu | Ile | Cys | Gly | Asp | Glu | |
| | 30 | | | | | 35 | | | | | 40 | | | | | |

| att | ggc | cta | act | gtg | gat | ggt | gat | ttg | ttt | gtg | gct | tgc | aat | gag | tgt | 197 |
|---|---|---|---|---|---|---|---|---|---|---|---|---|---|---|---|---|
| Ile | Gly | Leu | Thr | Val | Asp | Gly | Asp | Leu | Phe | Val | Ala | Cys | Asn | Glu | Cys | |
| 45 | | | | | 50 | | | | | 55 | | | | | | |

| ggt | ttt | cct | gtg | tgt | aga | cca | tgc | tac | gag | tat | gaa | aga | aga | gaa | ggg | 245 |
|---|---|---|---|---|---|---|---|---|---|---|---|---|---|---|---|---|
| Gly | Phe | Pro | Val | Cys | Arg | Pro | Cys | Tyr | Glu | Tyr | Glu | Arg | Arg | Glu | Gly | |
| 60 | | | | 65 | | | | | 70 | | | | | 75 | | |

| act | caa | aac | tgt | ccc | cag | tgc | aag | act | aga | tac | aag | cgt | ctc | aaa | ggg | 293 |
|---|---|---|---|---|---|---|---|---|---|---|---|---|---|---|---|---|
| Thr | Gln | Asn | Cys | Pro | Gln | Cys | Lys | Thr | Arg | Tyr | Lys | Arg | Leu | Lys | Gly | |
| | | | 80 | | | | | 85 | | | | | 90 | | | |

| agt | cca | agg | gtg | gag | gga | gat | gat | gaa | gaa | gat | gat | gtg | gat | gat | att | 341 |
|---|---|---|---|---|---|---|---|---|---|---|---|---|---|---|---|---|
| Ser | Pro | Arg | Val | Glu | Gly | Asp | Asp | Glu | Glu | Asp | Asp | Val | Asp | Asp | Ile | |
| | | 95 | | | | | 100 | | | | | 105 | | | | |

| gaa | cat | gag | ttc | atc | att | gaa | gat | gag | caa | gac | aag | aat | aag | cat | ctc | 389 |
|---|---|---|---|---|---|---|---|---|---|---|---|---|---|---|---|---|
| Glu | His | Glu | Phe | Ile | Ile | Glu | Asp | Glu | Gln | Asp | Lys | Asn | Lys | His | Leu | |
| | | | 110 | | | | | 115 | | | | | 120 | | | |

| act | gag | gca | atg | ctt | cat | ggg | aaa | atg | act | tac | gga | aga | ggc | cat | gat | 437 |
|---|---|---|---|---|---|---|---|---|---|---|---|---|---|---|---|---|
| Thr | Glu | Ala | Met | Leu | His | Gly | Lys | Met | Thr | Tyr | Gly | Arg | Gly | His | Asp | |
| | 125 | | | | | 130 | | | | | 135 | | | | | |

| gat | gaa | gaa | aat | agc | caa | ttc | cca | cca | gtt | ata | act | gga | atc | aga | tca | 485 |
|---|---|---|---|---|---|---|---|---|---|---|---|---|---|---|---|---|
| Asp | Glu | Glu | Asn | Ser | Gln | Phe | Pro | Pro | Val | Ile | Thr | Gly | Ile | Arg | Ser | |
| 140 | | | | | 145 | | | | | 150 | | | | | 155 | |

| agg | cct | gtg | agt | gga | gag | ttc | tcc | att | gga | tct | cat | gga | gaa | cag | atg | 533 |
|---|---|---|---|---|---|---|---|---|---|---|---|---|---|---|---|---|
| Arg | Pro | Val | Ser | Gly | Glu | Phe | Ser | Ile | Gly | Ser | His | Gly | Glu | Gln | Met | |
| | | | 160 | | | | | 165 | | | | | 170 | | | |

| cta | tct | tct | tca | ctt | cat | aag | aga | gtg | cac | cca | tat | cca | gtt | tct | gaa | 581 |
|---|---|---|---|---|---|---|---|---|---|---|---|---|---|---|---|---|
| Leu | Ser | Ser | Ser | Leu | His | Lys | Arg | Val | His | Pro | Tyr | Pro | Val | Ser | Glu | |
| | | | 175 | | | | | 180 | | | | | 185 | | | |

| cct | gga | agt | gca | aga | tgg | gac | gaa | aag | aaa | gag | gga | ggg | tgg | aaa | gag | 629 |
|---|---|---|---|---|---|---|---|---|---|---|---|---|---|---|---|---|
| Pro | Gly | Ser | Ala | Arg | Trp | Asp | Glu | Lys | Lys | Glu | Gly | Gly | Trp | Lys | Glu | |
| | | 190 | | | | | 195 | | | | | 200 | | | | |

| cgg | atg | gac | gag | tgg | aaa | atg | cag | cat | gga | aat | ctg | ggg | cct | gaa | caa | 677 |
|---|---|---|---|---|---|---|---|---|---|---|---|---|---|---|---|---|
| Arg | Met | Asp | Glu | Trp | Lys | Met | Gln | His | Gly | Asn | Leu | Gly | Pro | Glu | Gln | |
| | 205 | | | | | 210 | | | | | 215 | | | | | |

| gat | gac | gat | gca | gaa | gca | gcc | atg | tta | gaa | gat | gca | aga | cag | cca | ctc | 725 |
|---|---|---|---|---|---|---|---|---|---|---|---|---|---|---|---|---|
| Asp | Asp | Asp | Ala | Glu | Ala | Ala | Met | Leu | Glu | Asp | Ala | Arg | Gln | Pro | Leu | |
| 220 | | | | | 225 | | | | | 230 | | | | | 235 | |

| tcc | agg | aaa | gtt | cct | att | gca | tcc | agc | aag | atc | aat | ccg | tat | aga | atg | 773 |
|---|---|---|---|---|---|---|---|---|---|---|---|---|---|---|---|---|
| Ser | Arg | Lys | Val | Pro | Ile | Ala | Ser | Ser | Lys | Ile | Asn | Pro | Tyr | Arg | Met | |
| | | | 240 | | | | | 245 | | | | | 250 | | | |

| gtt | att | gtt | gct | agg | cta | atc | ata | ctg | gcc | gtc | ttt | ctt | cgc | tat | cga | 821 |
|---|---|---|---|---|---|---|---|---|---|---|---|---|---|---|---|---|

```
Val Ile Val Ala Arg Leu Ile Ile Leu Ala Val Phe Leu Arg Tyr Arg
            255                 260                 265 att ttg cat ccg gtg cat gac gca ctt ggg ctc tgg ctg aca tct ata      869
Ile Leu His Pro Val His Asp Ala Leu Gly Leu Trp Leu Thr Ser Ile
            270                 275                 280 gtc tgc gaa atc tgg ttt gca att tca tgg atc ctt gat caa ttc ccc      917
Val Cys Glu Ile Trp Phe Ala Ile Ser Trp Ile Leu Asp Gln Phe Pro
            285                 290                 295 aag tgg ttg cca atc gat cgc gag act tat ctg gat cgc ctt tct ctc      965
Lys Trp Leu Pro Ile Asp Arg Glu Thr Tyr Leu Asp Arg Leu Ser Leu
300                 305                 310                 315 agg tat gag cag gaa ggc ggg ccc aat atg ctt gct cca gtg gat gtc     1013
Arg Tyr Glu Gln Glu Gly Gly Pro Asn Met Leu Ala Pro Val Asp Val
                320                 325                 330 ttt gtc agt acc gtg gat cca atg aaa gaa ccc cct cta gtc acg ggc     1061
Phe Val Ser Thr Val Asp Pro Met Lys Glu Pro Pro Leu Val Thr Gly
            335                 340                 345 aac aca ctt tta tca att ttg gcc atg gac tat cca gtt gaa aag atc     1109
Asn Thr Leu Leu Ser Ile Leu Ala Met Asp Tyr Pro Val Glu Lys Ile
            350                 355                 360 tca tgt tac cta tct gac gac ggc gct tca atg tgc acc ttt gaa gcc     1157
Ser Cys Tyr Leu Ser Asp Asp Gly Ala Ser Met Cys Thr Phe Glu Ala
365                 370                 375 atg tct gaa act gct gaa ttt gct cga aaa tgg gtg cca ttc tgc aag     1205
Met Ser Glu Thr Ala Glu Phe Ala Arg Lys Trp Val Pro Phe Cys Lys
380                 385                 390                 395 aaa ttt aac ata gaa cca cga gcc cct gag ttt tac ttc act cta aag     1253
Lys Phe Asn Ile Glu Pro Arg Ala Pro Glu Phe Tyr Phe Thr Leu Lys
                400                 405                 410 gtt gat tac ctc aag gac aaa gtt cag cca acc ttt gtt aag gaa cgt     1301
Val Asp Tyr Leu Lys Asp Lys Val Gln Pro Thr Phe Val Lys Glu Arg
            415                 420                 425 cga gct atg aag aga gaa tat gaa gaa ttc aag gtt cgg ata aat gcg     1349
Arg Ala Met Lys Arg Glu Tyr Glu Glu Phe Lys Val Arg Ile Asn Ala
            430                 435                 440 att gta gca aaa gca cag aag gtt cct aca gag ggg tgg att atg caa     1397
Ile Val Ala Lys Ala Gln Lys Val Pro Thr Glu Gly Trp Ile Met Gln
            445                 450                 455 gat gga aca cca tgg cct gga aac aat acg agg gat cac cct ggt atg     1445
Asp Gly Thr Pro Trp Pro Gly Asn Asn Thr Arg Asp His Pro Gly Met
460                 465                 470                 475 att caa gta ttt ctc ggt cac agt gga gga cat gac gtt gaa ggg aac     1493
Ile Gln Val Phe Leu Gly His Ser Gly Gly His Asp Val Glu Gly Asn
                480                 485                 490 gag ctc cct cgc ctt gta tat gta tct cga gag aag agg cct ggt ttt     1541
Glu Leu Pro Arg Leu Val Tyr Val Ser Arg Glu Lys Arg Pro Gly Phe
            495                 500                 505 tca cat cat aaa aaa gcc ggc gcc atg aat gcc ctg att cgg gtt ctc     1589
Ser His His Lys Lys Ala Gly Ala Met Asn Ala Leu Ile Arg Val Leu
            510                 515                 520 gcc ata ctt acc aat gct cct ttc atg ctg aac ttg gat tgc gac cat     1637
Ala Ile Leu Thr Asn Ala Pro Phe Met Leu Asn Leu Asp Cys Asp His
            525                 530                 535 tat gta aat aat agc aag gcc gtt cga gag gct atg tgt ttc ttg atg     1685
Tyr Val Asn Asn Ser Lys Ala Val Arg Glu Ala Met Cys Phe Leu Met
540                 545                 550                 555 gac ccc cag att gga aag aga gtt tgc tac gtg caa ttt cct caa aga     1733
Asp Pro Gln Ile Gly Lys Arg Val Cys Tyr Val Gln Phe Pro Gln Arg
                560                 565                 570 ttt gat ggc att gat aca cat gat cga tac gcc aac aga aac act gtt     1781
```

```
                                                       -continued

Phe Asp Gly Ile Asp Thr His Asp Arg Tyr Ala Asn Arg Asn Thr Val
            575                 580                 585 ttc ttc gat att aac atg aag gga cta gat gga att cag ggt cca gtg      1829
Phe Phe Asp Ile Asn Met Lys Gly Leu Asp Gly Ile Gln Gly Pro Val
        590                 595                 600 tat gtg ggc aca gga tgc gtt ttc aaa agg caa gct ttg tat ggc tat      1877
Tyr Val Gly Thr Gly Cys Val Phe Lys Arg Gln Ala Leu Tyr Gly Tyr
    605                 610                 615 gac cct ccc aag gat cca aag cgc cca aag atg gaa acc tgc gac tgc      1925
Asp Pro Pro Lys Asp Pro Lys Arg Pro Lys Met Glu Thr Cys Asp Cys
620                 625                 630                 635 tgc cca tgt ttt gga cgt cgc aaa aag aag aat gct aag act ggt gca      1973
Cys Pro Cys Phe Gly Arg Arg Lys Lys Lys Asn Ala Lys Thr Gly Ala
                640                 645                 650 gtt gta gaa gga atg gat aat aat gac aag gag ctg ttg atg tcc cac      2021
Val Val Glu Gly Met Asp Asn Asn Asp Lys Glu Leu Leu Met Ser His
            655                 660                 665 atg aat ttt gaa aag aag ttt gga caa tca gca att ttc gta act tca      2069
Met Asn Phe Glu Lys Lys Phe Gly Gln Ser Ala Ile Phe Val Thr Ser
        670                 675                 680 act tta atg gaa gaa ggt ggt gta cct cct tcc tcg agt ccg gca gct      2117
Thr Leu Met Glu Glu Gly Gly Val Pro Pro Ser Ser Ser Pro Ala Ala
    685                 690                 695 ctg cta aag gaa gcc atc cat gtg atc agt tgt gga tat gaa gac aaa      2165
Leu Leu Lys Glu Ala Ile His Val Ile Ser Cys Gly Tyr Glu Asp Lys
700                 705                 710                 715 act gaa tgg gga ctc gag ctg ggc tgg att tac ggt tcg atc acg gag      2213
Thr Glu Trp Gly Leu Glu Leu Gly Trp Ile Tyr Gly Ser Ile Thr Glu
                720                 725                 730 gat att ctg aca ggt ttt aag atg cat tgt cgt ggc tgg agg tct att      2261
Asp Ile Leu Thr Gly Phe Lys Met His Cys Arg Gly Trp Arg Ser Ile
            735                 740                 745 tac tgt atg cca aag aga gct gca ttt aag ggt tca gct ccc atc aat      2309
Tyr Cys Met Pro Lys Arg Ala Ala Phe Lys Gly Ser Ala Pro Ile Asn
        750                 755                 760 cta tca gat cgg cta aac caa gtg ctc cgc tgg gct ctt gga tct gtt      2357
Leu Ser Asp Arg Leu Asn Gln Val Leu Arg Trp Ala Leu Gly Ser Val
    765                 770                 775 gaa att ttt ttc agt ggt cac agc cct aat tgg tat ggc tac aag aaa      2405
Glu Ile Phe Phe Ser Gly His Ser Pro Asn Trp Tyr Gly Tyr Lys Lys
780                 785                 790                 795 gga aag ctc aag tgg ctc gag agg ttt gcg tat gtg aac aca act atc      2453
Gly Lys Leu Lys Trp Leu Glu Arg Phe Ala Tyr Val Asn Thr Thr Ile
                800                 805                 810 tac ccc ttc acc tcc tta gca ctc gtt gca tac tgt tgc ctc cct gcc      2501
Tyr Pro Phe Thr Ser Leu Ala Leu Val Ala Tyr Cys Cys Leu Pro Ala
            815                 820                 825 atc tgc ctg ctt act gat aaa ttt atc atg ccc gag ata agc acc ttt      2549
Ile Cys Leu Leu Thr Asp Lys Phe Ile Met Pro Glu Ile Ser Thr Phe
        830                 835                 840 gca agt ctt ttc ttc att gcc ttg ttt ttg tca atc ttt tcc acg ggc      2597
Ala Ser Leu Phe Phe Ile Ala Leu Phe Leu Ser Ile Phe Ser Thr Gly
    845                 850                 855 att ctt gag ctc aga tgg agc gga gta agc att gag gaa tgg tgg aga      2645
Ile Leu Glu Leu Arg Trp Ser Gly Val Ser Ile Glu Glu Trp Trp Arg
860                 865                 870                 875 aac gag caa ttc tgg gtt ata ggt ggt gtg tct gct cac ctc ttt gct      2693
Asn Glu Gln Phe Trp Val Ile Gly Gly Val Ser Ala His Leu Phe Ala
                880                 885                 890 gtt gtc caa ggt ctt ctg aaa gtt tta gca ggt atc gac cta aac ttc      2741
```

-continued

```
Val Val Gln Gly Leu Leu Lys Val Leu Ala Gly Ile Asp Leu Asn Phe
            895                 900                 905 act gtc aca tcc aag gct aca gac gat gac gat ttt gga gag ctt tat      2789
Thr Val Thr Ser Lys Ala Thr Asp Asp Asp Asp Phe Gly Glu Leu Tyr
            910                 915                 920 gcc ttt aaa tgg aca acc ctg ctt atc cct cca acc act atc tta atc      2837
Ala Phe Lys Trp Thr Thr Leu Leu Ile Pro Pro Thr Thr Ile Leu Ile
            925                 930                 935 atc aac ctt gtt gga gtt gtt gct gga gtc tca gat gcc ata aac aat      2885
Ile Asn Leu Val Gly Val Val Ala Gly Val Ser Asp Ala Ile Asn Asn
940                 945                 950                 955 ggg tac cag tca tgg gga cct cta ttc ggg aag ctc ttc ttt gcc ttc      2933
Gly Tyr Gln Ser Trp Gly Pro Leu Phe Gly Lys Leu Phe Phe Ala Phe
                960                 965                 970 tgg gtg att gtc cat ctc tac cca ttc ctc aaa ggt cta atg ggg agg      2981
Trp Val Ile Val His Leu Tyr Pro Phe Leu Lys Gly Leu Met Gly Arg
            975                 980                 985 caa aac agg aca ccg act att gtg gtt ata tgg tca gtg ctc ctg gct      3029
Gln Asn Arg Thr Pro Thr Ile Val Val Ile Trp Ser Val Leu Leu Ala
            990                 995                 1000 tcc atc ttc tcc ttg ctt tgg gtc cgg att gat cca ttt gtg atg           3074
Ser Ile Phe Ser Leu Leu Trp Val Arg Ile Asp Pro Phe Val Met
    1005                1010                1015 aaa acc agg gga cct gac acc aag caa tgt gga ctc aac tgt taa           3119
Lys Thr Arg Gly Pro Asp Thr Lys Gln Cys Gly Leu Asn Cys
    1020                1025                1030 aagtgtgttt attttctagt tgatttgtgc atcatataga agatacatgt gcatcctgct    3179
tctaaggaaa tacgatatgc gatgtataaa ctgactaaga tggagatgct acaaggaata   3239
aagttagagt gaaatttttg tgtaaaaaaa aaaaaaaa                             3277

<210> SEQ ID NO 4
<211> LENGTH: 1032
<212> TYPE: PRT
<213> ORGANISM: Populus tremuloides

<400> SEQUENCE: 4

Met Glu Ala Ser Ala Gly Leu Val Ala Gly Ser His Asn Arg Asn Glu
1               5                   10                  15

Leu Val Val Ile His Gly His Glu Glu His Lys Pro Leu Lys Asn Leu
            20                  25                  30

Asp Gly Gln Val Cys Glu Ile Cys Gly Asp Glu Ile Gly Leu Thr Val
        35                  40                  45

Asp Gly Asp Leu Phe Val Ala Cys Asn Glu Cys Gly Phe Pro Val Cys
    50                  55                  60

Arg Pro Cys Tyr Glu Tyr Glu Arg Arg Glu Gly Thr Gln Asn Cys Pro
65                  70                  75                  80

Gln Cys Lys Thr Arg Tyr Lys Arg Leu Lys Gly Ser Pro Arg Val Glu
                85                  90                  95

Gly Asp Asp Glu Glu Asp Asp Val Asp Ile Glu His Glu Phe Ile
            100                 105                 110

Ile Glu Asp Glu Gln Asp Lys Asn Lys His Leu Thr Glu Ala Met Leu
        115                 120                 125

His Gly Lys Met Thr Tyr Gly Arg Gly His Asp Asp Glu Glu Asn Ser
    130                 135                 140

Gln Phe Pro Pro Val Ile Thr Gly Ile Arg Ser Arg Pro Val Ser Gly
145                 150                 155                 160

Glu Phe Ser Ile Gly Ser His Gly Glu Gln Met Leu Ser Ser Ser Leu
```

```
                165                 170                 175
His Lys Arg Val His Pro Tyr Pro Val Ser Glu Pro Gly Ser Ala Arg
                180                 185                 190

Trp Asp Glu Lys Lys Glu Gly Gly Trp Lys Glu Arg Met Asp Glu Trp
                195                 200                 205

Lys Met Gln His Gly Asn Leu Gly Pro Glu Gln Asp Asp Ala Glu
                210                 215                 220

Ala Ala Met Leu Glu Asp Ala Arg Gln Pro Leu Ser Arg Lys Val Pro
225                 230                 235                 240

Ile Ala Ser Ser Lys Ile Asn Pro Tyr Arg Met Val Ile Val Ala Arg
                245                 250                 255

Leu Ile Ile Leu Ala Val Phe Leu Arg Tyr Arg Ile Leu His Pro Val
                260                 265                 270

His Asp Ala Leu Gly Leu Trp Leu Thr Ser Ile Val Cys Glu Ile Trp
                275                 280                 285

Phe Ala Ile Ser Trp Ile Leu Asp Gln Phe Pro Lys Trp Leu Pro Ile
                290                 295                 300

Asp Arg Glu Thr Tyr Leu Asp Arg Leu Ser Leu Arg Tyr Glu Gln Glu
305                 310                 315                 320

Gly Gly Pro Asn Met Leu Ala Pro Val Asp Val Phe Val Ser Thr Val
                325                 330                 335

Asp Pro Met Lys Glu Pro Pro Leu Val Thr Gly Asn Thr Leu Leu Ser
                340                 345                 350

Ile Leu Ala Met Asp Tyr Pro Val Glu Lys Ile Ser Cys Tyr Leu Ser
                355                 360                 365

Asp Asp Gly Ala Ser Met Cys Thr Phe Glu Ala Met Ser Glu Thr Ala
                370                 375                 380

Glu Phe Ala Arg Lys Trp Val Pro Phe Cys Lys Lys Phe Asn Ile Glu
385                 390                 395                 400

Pro Arg Ala Pro Glu Phe Tyr Phe Thr Leu Lys Val Asp Tyr Leu Lys
                405                 410                 415

Asp Lys Val Gln Pro Thr Phe Val Lys Glu Arg Arg Ala Met Lys Arg
                420                 425                 430

Glu Tyr Glu Glu Phe Lys Val Arg Ile Asn Ala Ile Val Ala Lys Ala
                435                 440                 445

Gln Lys Val Pro Thr Glu Gly Trp Ile Met Gln Asp Gly Thr Pro Trp
                450                 455                 460

Pro Gly Asn Asn Thr Arg Asp His Pro Gly Met Ile Gln Val Phe Leu
465                 470                 475                 480

Gly His Ser Gly Gly His Asp Val Glu Gly Asn Glu Leu Pro Arg Leu
                485                 490                 495

Val Tyr Val Ser Arg Glu Lys Arg Pro Gly Phe Ser His His Lys Lys
                500                 505                 510

Ala Gly Ala Met Asn Ala Leu Ile Arg Val Leu Ala Ile Leu Thr Asn
                515                 520                 525

Ala Pro Phe Met Leu Asn Leu Asp Cys Asp His Tyr Val Asn Asn Ser
530                 535                 540

Lys Ala Val Arg Glu Ala Met Cys Phe Leu Met Asp Pro Gln Ile Gly
545                 550                 555                 560

Lys Arg Val Cys Tyr Val Gln Phe Pro Gln Arg Phe Asp Gly Ile Asp
                565                 570                 575

Thr His Asp Arg Tyr Ala Asn Arg Asn Thr Val Phe Phe Asp Ile Asn
                580                 585                 590
```

-continued

```
Met Lys Gly Leu Asp Gly Ile Gln Gly Pro Val Tyr Gly Thr Gly
            595                 600                 605

Cys Val Phe Lys Arg Gln Ala Leu Tyr Gly Tyr Pro Pro Lys Asp
610                 615                 620

Pro Lys Arg Pro Lys Met Glu Thr Cys Asp Cys Pro Cys Phe Gly
625                 630                 635                 640

Arg Arg Lys Lys Lys Asn Ala Lys Thr Gly Ala Val Val Glu Gly Met
                645                 650                 655

Asp Asn Asn Asp Lys Glu Leu Leu Met Ser His Met Asn Phe Glu Lys
                660                 665                 670

Lys Phe Gly Gln Ser Ala Ile Phe Val Thr Ser Thr Leu Met Glu Glu
            675                 680                 685

Gly Gly Val Pro Pro Ser Ser Ser Pro Ala Ala Leu Leu Lys Glu Ala
690                 695                 700

Ile His Val Ile Ser Cys Gly Tyr Glu Asp Lys Thr Glu Trp Gly Leu
705                 710                 715                 720

Glu Leu Gly Trp Ile Tyr Gly Ser Ile Thr Glu Asp Ile Leu Thr Gly
                725                 730                 735

Phe Lys Met His Cys Arg Gly Trp Arg Ser Ile Tyr Cys Met Pro Lys
            740                 745                 750

Arg Ala Ala Phe Lys Gly Ser Ala Pro Ile Asn Leu Ser Asp Arg Leu
            755                 760                 765

Asn Gln Val Leu Arg Trp Ala Leu Gly Ser Val Glu Ile Phe Phe Ser
770                 775                 780

Gly His Ser Pro Asn Trp Tyr Gly Tyr Lys Lys Gly Lys Leu Lys Trp
785                 790                 795                 800

Leu Glu Arg Phe Ala Tyr Val Asn Thr Thr Ile Tyr Pro Phe Thr Ser
                805                 810                 815

Leu Ala Leu Val Ala Tyr Cys Cys Leu Pro Ala Ile Cys Leu Leu Thr
                820                 825                 830

Asp Lys Phe Ile Met Pro Glu Ile Ser Thr Phe Ala Ser Leu Phe Phe
            835                 840                 845

Ile Ala Leu Phe Leu Ser Ile Phe Ser Thr Gly Ile Leu Glu Leu Arg
850                 855                 860

Trp Ser Gly Val Ser Ile Glu Glu Trp Trp Arg Asn Glu Gln Phe Trp
865                 870                 875                 880

Val Ile Gly Gly Val Ser Ala His Leu Phe Ala Val Val Gln Gly Leu
                885                 890                 895

Leu Lys Val Leu Ala Gly Ile Asp Leu Asn Phe Thr Val Thr Ser Lys
            900                 905                 910

Ala Thr Asp Asp Asp Phe Gly Glu Leu Tyr Ala Phe Lys Trp Thr
            915                 920                 925

Thr Leu Leu Ile Pro Pro Thr Thr Ile Leu Ile Ile Asn Leu Val Gly
            930                 935                 940

Val Val Ala Gly Val Ser Asp Ala Ile Asn Asn Gly Tyr Gln Ser Trp
945                 950                 955                 960

Gly Pro Leu Phe Gly Lys Leu Phe Phe Ala Phe Trp Val Ile Val His
                965                 970                 975

Leu Tyr Pro Phe Leu Lys Gly Leu Met Gly Arg Gln Asn Arg Thr Pro
            980                 985                 990

Thr Ile Val Val Ile Trp Ser Val Leu Leu Ala Ser Ile Phe Ser Leu
            995                 1000                1005

Leu Trp Val Arg Ile Asp Pro Phe Val Met Lys Thr Arg Gly Pro
        1010                1015                1020
```

```
Asp Thr Lys Gln Cys Gly Leu Asn Cys
    1025                1030

<210> SEQ ID NO 5
<211> LENGTH: 3401
<212> TYPE: DNA
<213> ORGANISM: Populus tremuloides
<220> FEATURE:
<221> NAME/KEY: CDS
<222> LOCATION: (39)..(3167)

<400> SEQUENCE: 5
gagaactagt ctcgactttt ttttccttgc tgttgtcc atg gct ggc ctt gtc acg      56
                                          Met Ala Gly Leu Val Thr
                                            1               5 ggc agt tca cag acc ttg cat gcc aaa gat gag ctg agg cct cca act       104
Gly Ser Ser Gln Thr Leu His Ala Lys Asp Glu Leu Arg Pro Pro Thr
            10                  15                  20 cgc cag tct gca acg tcg aaa aaa tgt aga gtt tgt ggg gat gag att       152
Arg Gln Ser Ala Thr Ser Lys Lys Cys Arg Val Cys Gly Asp Glu Ile
        25                  30                  35 gga gtt aag gaa gat gga gag gtg ttt gtt gct tgt cat gtg tgt ggc       200
Gly Val Lys Glu Asp Gly Glu Val Phe Val Ala Cys His Val Cys Gly
    40                  45                  50 ttt cct gtt tgt agg cct tgt tat gag tat gag agg agt gaa ggc aac       248
Phe Pro Val Cys Arg Pro Cys Tyr Glu Tyr Glu Arg Ser Glu Gly Asn
55                  60                  65                  70 cag tcc tgt cct cag tgc aac act cga tat aag cgt cac aaa ggt tgt       296
Gln Ser Cys Pro Gln Cys Asn Thr Arg Tyr Lys Arg His Lys Gly Cys
                75                  80                  85 cct aga gtt cct gga gat aat gac gat gag gat gcc aat ttt gat gat       344
Pro Arg Val Pro Gly Asp Asn Asp Asp Glu Asp Ala Asn Phe Asp Asp
            90                  95                  100 ttt gac gac gaa ttt cag att aag cat cat gat cat gat gaa tcc aat       392
Phe Asp Asp Glu Phe Gln Ile Lys His His Asp His Asp Glu Ser Asn
        105                 110                 115 cag aaa aat gtt ttt agt cgc acg gaa att gag cac tac aat gaa cag       440
Gln Lys Asn Val Phe Ser Arg Thr Glu Ile Glu His Tyr Asn Glu Gln
    120                 125                 130 gaa atg cac ccc att cgt ccg gcc ttt tcg tca gca gga agt gtt gct       488
Glu Met His Pro Ile Arg Pro Ala Phe Ser Ser Ala Gly Ser Val Ala
135                 140                 145                 150 gga aag gat ctt gaa ggc gag aaa gag ggt tat agc aat gca gaa tgg       536
Gly Lys Asp Leu Glu Gly Glu Lys Glu Gly Tyr Ser Asn Ala Glu Trp
                155                 160                 165 caa gag agg gtg gag aaa tgg aaa gtt agg caa gaa aag aga ggt ttg       584
Gln Glu Arg Val Glu Lys Trp Lys Val Arg Gln Glu Lys Arg Gly Leu
            170                 175                 180 gtg agc aaa gat gat gga gga aat gat caa gga gag gaa gat gag tac       632
Val Ser Lys Asp Asp Gly Gly Asn Asp Gln Gly Glu Glu Asp Glu Tyr
        185                 190                 195 ctt atg gct gaa gcc agg caa cca cta tgg aga aaa atc cca att ccc       680
Leu Met Ala Glu Ala Arg Gln Pro Leu Trp Arg Lys Ile Pro Ile Pro
    200                 205                 210 tcg agc aga atc aac ccg tat cga att gtc att gtc ctt cga ctt atc       728
Ser Ser Arg Ile Asn Pro Tyr Arg Ile Val Ile Val Leu Arg Leu Ile
215                 220                 225                 230 att ctt tgc ttc ttt ttc cgt ttt tgg atc tta act cca gca tct gat       776
Ile Leu Cys Phe Phe Phe Arg Phe Trp Ile Leu Thr Pro Ala Ser Asp
                235                 240                 245 gct tat gca ttg ggg ctt atc tct gta ata tgt gag gta tgg ttt ggc       824
```

```
                 Ala Tyr Ala Leu Gly Leu Ile Ser Val Ile Cys Glu Val Trp Phe Gly
                         250                 255                 260 ctc tcc tgg atc ttg gac cag ttc cca aaa tgg aac ccc att gaa cgt      872
Leu Ser Trp Ile Leu Asp Gln Phe Pro Lys Trp Asn Pro Ile Glu Arg
        265                 270                 275 gaa act tat ctc gat cgc cta tcc atg agg ttt gag cgt gag ggt gag      920
Glu Thr Tyr Leu Asp Arg Leu Ser Met Arg Phe Glu Arg Glu Gly Glu
        280                 285                 290 cct aat cgc ctg ggc cca gtt gat gtg ttt gtg agt act gtg gat cct      968
Pro Asn Arg Leu Gly Pro Val Asp Val Phe Val Ser Thr Val Asp Pro
295                 300                 305                 310 ctc aag gaa cca cca ata ata act gca aat aca gtc ctt tca atc cta     1016
Leu Lys Glu Pro Pro Ile Ile Thr Ala Asn Thr Val Leu Ser Ile Leu
                315                 320                 325 tcc gtt gat tat cct gtc gac aag gtc agt tgt tat gta tca gat gat     1064
Ser Val Asp Tyr Pro Val Asp Lys Val Ser Cys Tyr Val Ser Asp Asp
                330                 335                 340 ggt gca tcc atg ctc ctt ttc gac tcc ctg gca gaa act gct gag ttt     1112
Gly Ala Ser Met Leu Leu Phe Asp Ser Leu Ala Glu Thr Ala Glu Phe
            345                 350                 355 gct aga agg tgg gtt cca ttt tgc aag aag cat aac att gag cca agg     1160
Ala Arg Arg Trp Val Pro Phe Cys Lys Lys His Asn Ile Glu Pro Arg
        360                 365                 370 gct cct gag ttc tac ttc act cag aag att gac tac ttg aaa gac aaa     1208
Ala Pro Glu Phe Tyr Phe Thr Gln Lys Ile Asp Tyr Leu Lys Asp Lys
375                 380                 385                 390 gtg cat ccc aac ttt gtg aag gag cgc aga gct atg aaa aga gaa tat     1256
Val His Pro Asn Phe Val Lys Glu Arg Arg Ala Met Lys Arg Glu Tyr
                395                 400                 405 gaa gaa ttc aaa gta agg atc aac gca ttg gtg tca aag gcc caa aag     1304
Glu Glu Phe Lys Val Arg Ile Asn Ala Leu Val Ser Lys Ala Gln Lys
                410                 415                 420 aaa cca gaa gaa gga tgg gtg atg cag gat ggt acc cca tgg cct gga     1352
Lys Pro Glu Glu Gly Trp Val Met Gln Asp Gly Thr Pro Trp Pro Gly
            425                 430                 435 aac atc acc cgt gat cat cct gga atg att cag gta tat cta gga agt     1400
Asn Ile Thr Arg Asp His Pro Gly Met Ile Gln Val Tyr Leu Gly Ser
        440                 445                 450 gag ggt gcg ctc gac gtg gaa ggc aag gag ctt ccg agg ctt gtg tat     1448
Glu Gly Ala Leu Asp Val Glu Gly Lys Glu Leu Pro Arg Leu Val Tyr
455                 460                 465                 470 gtt tcc cgt gag aaa cga cct gga tat aac cac cac aag aaa gca ggt     1496
Val Ser Arg Glu Lys Arg Pro Gly Tyr Asn His His Lys Lys Ala Gly
                475                 480                 485 gcc atg aat gct ctg att cga gtc tca gca gtg ctc acc aat gca cct     1544
Ala Met Asn Ala Leu Ile Arg Val Ser Ala Val Leu Thr Asn Ala Pro
                490                 495                 500 ttt atg ttg aat ttg gat tgt gac cat tac atc aat aac agc aag gct     1592
Phe Met Leu Asn Leu Asp Cys Asp His Tyr Ile Asn Asn Ser Lys Ala
            505                 510                 515 gta aga gaa gcc atg tgc ttt ttg atg gat ccc caa ctt ggg aag aag     1640
Val Arg Glu Ala Met Cys Phe Leu Met Asp Pro Gln Leu Gly Lys Lys
        520                 525                 530 ctc tgc tat gtc cag ttt ccg cag agg ttt gat ggt atc gat cgc cat     1688
Leu Cys Tyr Val Gln Phe Pro Gln Arg Phe Asp Gly Ile Asp Arg His
535                 540                 545                 550 gat aga tat gct aat cgc aac gtt gtg ttc ttt gat ata aac atg aaa     1736
Asp Arg Tyr Ala Asn Arg Asn Val Val Phe Phe Asp Ile Asn Met Lys
                555                 560                 565 ggt cta gat ggg gtt caa ggg cca gta tat gtt ggt act gga tgt gtc     1784
```

```
            Gly Leu Asp Gly Val Gln Gly Pro Val Tyr Val Gly Thr Gly Cys Val
                    570                 575                 580 ttc aac agg cag tcc ttg tat ggc tat gat cct cca gtg tcc gag aag     1832
Phe Asn Arg Gln Ser Leu Tyr Gly Tyr Asp Pro Pro Val Ser Glu Lys
            585                 590                 595 aga ccc aag atg aca tgc gat tgc tgg cct tca tgg tgt tgc tgt tgc     1880
Arg Pro Lys Met Thr Cys Asp Cys Trp Pro Ser Trp Cys Cys Cys Cys
            600                 605                 610 ttt ggt ggt tca agg aaa aag tct aag aag aaa ggg caa aga agt ctt     1928
Phe Gly Gly Ser Arg Lys Lys Ser Lys Lys Lys Gly Gln Arg Ser Leu
615                 620                 625                 630 ctt gga gga cta tac ccc atc aaa aag aaa atg atg ggg aag aag tac     1976
Leu Gly Gly Leu Tyr Pro Ile Lys Lys Lys Met Met Gly Lys Lys Tyr
                    635                 640                 645 aca agg aaa gca tct gca cca gtc ttt gat ctt gaa gag att gaa gaa     2024
Thr Arg Lys Ala Ser Ala Pro Val Phe Asp Leu Glu Glu Ile Glu Glu
                650                 655                 660 ggg ctt gaa ggc tac gaa gag ttg gag aaa tca tca ctc atg tca caa     2072
Gly Leu Glu Gly Tyr Glu Glu Leu Glu Lys Ser Ser Leu Met Ser Gln
            665                 670                 675 aaa agt ttc gag aaa cgg ttt ggg caa tca ccg gta ttt att gcc tct     2120
Lys Ser Phe Glu Lys Arg Phe Gly Gln Ser Pro Val Phe Ile Ala Ser
680                 685                 690 acc ctc atg gaa aat ggt ggc gtg cct gaa gga act aac tct caa tca     2168
Thr Leu Met Glu Asn Gly Gly Val Pro Glu Gly Thr Asn Ser Gln Ser
695                 700                 705                 710 cac att aag gaa gcc att cat gtt ata agt tgc ggg tat gaa gaa aaa     2216
His Ile Lys Glu Ala Ile His Val Ile Ser Cys Gly Tyr Glu Glu Lys
                    715                 720                 725 acg gaa tgg ggt aaa gag gtt gga tgg att tat ggt tct gtt aca gaa     2264
Thr Glu Trp Gly Lys Glu Val Gly Trp Ile Tyr Gly Ser Val Thr Glu
                730                 735                 740 gat atc ctg aca ggc ttc aag atg cat tgt aga ggg tgg agg tct gtc     2312
Asp Ile Leu Thr Gly Phe Lys Met His Cys Arg Gly Trp Arg Ser Val
            745                 750                 755 tac tgt tct ccc cag aga cca gct ttt aag gga tct gct ccc att aat     2360
Tyr Cys Ser Pro Gln Arg Pro Ala Phe Lys Gly Ser Ala Pro Ile Asn
760                 765                 770 cta tca gat agg ttg cac caa gtt ctg cga tgg gca cta ggc tct att     2408
Leu Ser Asp Arg Leu His Gln Val Leu Arg Trp Ala Leu Gly Ser Ile
775                 780                 785                 790 gag att ttc ctt agt cat cac tgt cct cta tgg tat ggc tat ggg gga     2456
Glu Ile Phe Leu Ser His His Cys Pro Leu Trp Tyr Gly Tyr Gly Gly
                    795                 800                 805 aag ttg aag ttg ctg gag agg ctt gct tac atc aac acc atc gtt tac     2504
Lys Leu Lys Leu Leu Glu Arg Leu Ala Tyr Ile Asn Thr Ile Val Tyr
                810                 815                 820 cct ttc acc tcc att ccc tta ctt gcc tac tgt act att cca gca gtc     2552
Pro Phe Thr Ser Ile Pro Leu Leu Ala Tyr Cys Thr Ile Pro Ala Val
            825                 830                 835 tgc ctt ctg aca gga aaa ttt atc att cct act ctg aac aac ctt gct     2600
Cys Leu Leu Thr Gly Lys Phe Ile Ile Pro Thr Leu Asn Asn Leu Ala
840                 845                 850 agc ata tgg ttc cta ggc cct ttt cat ctc aat cat agc aac atc tgt     2648
Ser Ile Trp Phe Leu Gly Pro Phe His Leu Asn His Ser Asn Ile Cys
855                 860                 865                 870 gtt gga act tcg tgg agt gga gtc agc atc cag gac ttg tgg cgt aat     2696
Val Gly Thr Ser Trp Ser Gly Val Ser Ile Gln Asp Leu Trp Arg Asn
                    875                 880                 885 gag caa ttt tgg gtt atc ggc ggt gtc tca gct cat ctt ttt gcc gtc     2744
```

-continued

| | | |
|---|---|---|
| Glu Gln Phe Trp Val Ile Gly Gly Val Ser Ala His Leu Phe Ala Val<br>890 895 900 | | |
| ttc caa ggc ctc ctc aag gtc ctt gca gga gtt gac act aac ttc act<br>Phe Gln Gly Leu Leu Lys Val Leu Ala Gly Val Asp Thr Asn Phe Thr<br>905 910 915 | 2792 | |
| gtt aca tca aaa tca gca gac gat gcc gag ttt gga gag ctg tac ctc<br>Val Thr Ser Lys Ser Ala Asp Asp Ala Glu Phe Gly Glu Leu Tyr Leu<br>920 925 930 | 2840 | |
| ttc aaa tgg acc acc ctc ctc atc cca cca acc acc cta atc atc ttg<br>Phe Lys Trp Thr Thr Leu Leu Ile Pro Pro Thr Thr Leu Ile Ile Leu<br>935 940 945 950 | 2888 | |
| aat atg gtt gga gtt gta gca gga gta tcc gat gca ata aac aac gga<br>Asn Met Val Gly Val Val Ala Gly Val Ser Asp Ala Ile Asn Asn Gly<br>955 960 965 | 2936 | |
| tat gga tca tgg ggt cct tta ttt ggg aag cta ttt ttc gct ttc tgg<br>Tyr Gly Ser Trp Gly Pro Leu Phe Gly Lys Leu Phe Phe Ala Phe Trp<br>970 975 980 | 2984 | |
| gtc att gtc cat ctc tat cct ttc ctc aaa ggt ctg atg gga agg caa<br>Val Ile Val His Leu Tyr Pro Phe Leu Lys Gly Leu Met Gly Arg Gln<br>985 990 995 | 3032 | |
| aac agg act cct aca att gtt gtc ctc tgg tct ata ctt ctt gca<br>Asn Arg Thr Pro Thr Ile Val Val Leu Trp Ser Ile Leu Leu Ala<br>1000 1005 1010 | 3077 | |
| tct att ttc tca ttg att tgg gtt aga att gat ccc ttc ttg ccc<br>Ser Ile Phe Ser Leu Ile Trp Val Arg Ile Asp Pro Phe Leu Pro<br>1015 1020 1025 | 3122 | |
| aag caa act ggc cca att ctc aaa caa tgt gga gtg gag tgc tag<br>Lys Gln Thr Gly Pro Ile Leu Lys Gln Cys Gly Val Glu Cys<br>1030 1035 1040 | 3167 | |
| ctagtcaatg cctttgaat tttgaggtct gctcctgttc tgttctgtgt tttgagtctt | 3227 | |
| tcacaggtta tcccactttt gctcagttgt ttttccttt taatggggga gtggagtggt | 3287 | |
| cattgtatgg attatcagtg agattttct gttagcaagc aagcgtatgc acgcaaactt | 3347 | |
| taagaatttt attaattaag aattacttaa aaattaaaaa aaaaaaaaaa aaaa | 3401 | |

<210> SEQ ID NO 6
<211> LENGTH: 1042
<212> TYPE: PRT
<213> ORGANISM: Populus tremuloides

<400> SEQUENCE: 6

Met Ala Gly Leu Val Thr Gly Ser Ser Gln Thr Leu His Ala Lys Asp
1               5                   10                  15

Glu Leu Arg Pro Pro Thr Arg Gln Ser Ala Thr Ser Lys Lys Cys Arg
            20                  25                  30

Val Cys Gly Asp Glu Ile Gly Val Lys Glu Asp Gly Val Phe Val
        35                  40                  45

Ala Cys His Val Cys Gly Phe Pro Val Cys Arg Pro Cys Tyr Glu Tyr
    50                  55                  60

Glu Arg Ser Glu Gly Asn Gln Ser Cys Pro Gln Cys Asn Thr Arg Tyr
65                  70                  75                  80

Lys Arg His Lys Gly Cys Pro Arg Val Pro Gly Asp Asn Asp Glu
            85                  90                  95

Asp Ala Asn Phe Asp Asp Phe Asp Glu Phe Gln Ile Lys His His
                100                 105                 110

Asp His Asp Glu Ser Asn Gln Lys Asn Val Phe Ser Arg Thr Glu Ile
            115                 120                 125

Glu His Tyr Asn Glu Gln Glu Met His Pro Ile Arg Pro Ala Phe Ser

-continued

```
            130                 135                 140
Ser Ala Gly Ser Val Ala Gly Lys Asp Leu Glu Gly Glu Lys Glu Gly
145                 150                 155                 160

Tyr Ser Asn Ala Glu Trp Gln Glu Arg Val Glu Lys Trp Lys Val Arg
                165                 170                 175

Gln Glu Lys Arg Gly Leu Val Ser Lys Asp Asp Gly Gly Asn Asp Gln
                180                 185                 190

Gly Glu Glu Asp Glu Tyr Leu Met Ala Glu Ala Arg Gln Pro Leu Trp
                195                 200                 205

Arg Lys Ile Pro Ile Pro Ser Ser Arg Ile Asn Pro Tyr Arg Ile Val
210                 215                 220

Ile Val Leu Arg Leu Ile Ile Leu Cys Phe Phe Phe Arg Phe Trp Ile
225                 230                 235                 240

Leu Thr Pro Ala Ser Asp Ala Tyr Ala Leu Gly Leu Ile Ser Val Ile
                245                 250                 255

Cys Glu Val Trp Phe Gly Leu Ser Trp Ile Leu Asp Gln Phe Pro Lys
                260                 265                 270

Trp Asn Pro Ile Glu Arg Glu Thr Tyr Leu Asp Arg Leu Ser Met Arg
                275                 280                 285

Phe Glu Arg Glu Gly Glu Pro Asn Arg Leu Gly Pro Val Asp Val Phe
290                 295                 300

Val Ser Thr Val Asp Pro Leu Lys Glu Pro Ile Ile Thr Ala Asn
305                 310                 315                 320

Thr Val Leu Ser Ile Leu Ser Val Asp Tyr Pro Val Asp Lys Val Ser
                325                 330                 335

Cys Tyr Val Ser Asp Asp Gly Ala Ser Met Leu Leu Phe Asp Ser Leu
                340                 345                 350

Ala Glu Thr Ala Glu Phe Ala Arg Arg Trp Val Pro Phe Cys Lys Lys
                355                 360                 365

His Asn Ile Glu Pro Arg Ala Pro Glu Phe Tyr Phe Thr Gln Lys Ile
                370                 375                 380

Asp Tyr Leu Lys Asp Lys Val His Pro Asn Phe Val Lys Glu Arg Arg
385                 390                 395                 400

Ala Met Lys Arg Glu Tyr Glu Glu Phe Lys Val Arg Ile Asn Ala Leu
                405                 410                 415

Val Ser Lys Ala Gln Lys Lys Pro Glu Glu Gly Trp Val Met Gln Asp
                420                 425                 430

Gly Thr Pro Trp Pro Gly Asn Ile Thr Arg Asp His Pro Gly Met Ile
                435                 440                 445

Gln Val Tyr Leu Gly Ser Glu Gly Ala Leu Asp Val Glu Gly Lys Glu
                450                 455                 460

Leu Pro Arg Leu Val Tyr Val Ser Arg Glu Lys Arg Pro Gly Tyr Asn
465                 470                 475                 480

His His Lys Lys Ala Gly Ala Met Asn Ala Leu Ile Arg Val Ser Ala
                485                 490                 495

Val Leu Thr Asn Ala Pro Phe Met Leu Asn Leu Asp Cys Asp His Tyr
                500                 505                 510

Ile Asn Asn Ser Lys Ala Val Arg Glu Ala Met Cys Phe Leu Met Asp
                515                 520                 525

Pro Gln Leu Gly Lys Lys Leu Cys Tyr Val Gln Phe Pro Gln Arg Phe
                530                 535                 540

Asp Gly Ile Asp Arg His Asp Arg Tyr Ala Asn Arg Asn Val Val Phe
545                 550                 555                 560
```

-continued

Phe Asp Ile Asn Met Lys Gly Leu Asp Gly Val Gln Gly Pro Val Tyr
                565                 570                 575

Val Gly Thr Gly Cys Val Phe Asn Arg Gln Ser Leu Tyr Gly Tyr Asp
            580                 585                 590

Pro Pro Val Ser Glu Lys Arg Pro Lys Met Thr Cys Asp Cys Trp Pro
            595                 600                 605

Ser Trp Cys Cys Cys Cys Phe Gly Gly Ser Arg Lys Lys Ser Lys Lys
        610                 615                 620

Lys Gly Gln Arg Ser Leu Leu Gly Gly Leu Tyr Pro Ile Lys Lys Lys
625                 630                 635                 640

Met Met Gly Lys Lys Tyr Thr Arg Lys Ala Ser Ala Pro Val Phe Asp
                645                 650                 655

Leu Glu Glu Ile Glu Glu Gly Leu Glu Gly Tyr Glu Glu Leu Glu Lys
            660                 665                 670

Ser Ser Leu Met Ser Gln Lys Ser Phe Glu Lys Arg Phe Gly Gln Ser
        675                 680                 685

Pro Val Phe Ile Ala Ser Thr Leu Met Glu Asn Gly Gly Val Pro Glu
        690                 695                 700

Gly Thr Asn Ser Gln Ser His Ile Lys Glu Ala Ile His Val Ile Ser
705                 710                 715                 720

Cys Gly Tyr Glu Glu Lys Thr Glu Trp Gly Lys Glu Val Gly Trp Ile
                725                 730                 735

Tyr Gly Ser Val Thr Glu Asp Ile Leu Thr Gly Phe Lys Met His Cys
            740                 745                 750

Arg Gly Trp Arg Ser Val Tyr Cys Ser Pro Gln Arg Pro Ala Phe Lys
        755                 760                 765

Gly Ser Ala Pro Ile Asn Leu Ser Asp Arg Leu His Gln Val Leu Arg
        770                 775                 780

Trp Ala Leu Gly Ser Ile Glu Ile Phe Leu Ser His Cys Pro Leu
785                 790                 795                 800

Trp Tyr Gly Tyr Gly Gly Lys Leu Lys Leu Leu Glu Arg Leu Ala Tyr
                805                 810                 815

Ile Asn Thr Ile Val Tyr Pro Phe Thr Ser Ile Pro Leu Leu Ala Tyr
            820                 825                 830

Cys Thr Ile Pro Ala Val Cys Leu Leu Thr Gly Lys Phe Ile Ile Pro
        835                 840                 845

Thr Leu Asn Asn Leu Ala Ser Ile Trp Phe Leu Gly Pro Phe His Leu
850                 855                 860

Asn His Ser Asn Ile Cys Val Gly Thr Ser Trp Ser Gly Val Ser Ile
865                 870                 875                 880

Gln Asp Leu Trp Arg Asn Glu Gln Phe Trp Val Ile Gly Gly Val Ser
                885                 890                 895

Ala His Leu Phe Ala Val Phe Gln Gly Leu Leu Lys Val Leu Ala Gly
            900                 905                 910

Val Asp Thr Asn Phe Thr Val Thr Ser Lys Ser Ala Asp Asp Ala Glu
        915                 920                 925

Phe Gly Glu Leu Tyr Leu Phe Lys Trp Thr Thr Leu Leu Ile Pro Pro
        930                 935                 940

Thr Thr Leu Ile Ile Leu Asn Met Val Gly Val Val Ala Gly Val Ser
945                 950                 955                 960

Asp Ala Ile Asn Asn Gly Tyr Gly Ser Trp Gly Pro Leu Phe Gly Lys
                965                 970                 975

Leu Phe Phe Ala Phe Trp Val Ile Val His Leu Tyr Pro Phe Leu Lys
            980                 985                 990

Gly Leu Met Gly Arg Gln Asn Arg Thr Pro Thr Ile Val Val Leu Trp
            995                 1000                1005

Ser Ile Leu Leu Ala Ser Ile Phe Ser Leu Ile Trp Val Arg Ile
        1010                1015                1020

Asp Pro Phe Leu Pro Lys Gln Thr Gly Pro Ile Leu Lys Gln Cys
        1025                1030                1035

Gly Val Glu Cys
        1040

<210> SEQ ID NO 7
<211> LENGTH: 5
<212> TYPE: PRT
<213> ORGANISM: PtrCesA

<400> SEQUENCE: 7

Gln Val Leu Arg Trp
1               5

<210> SEQ ID NO 8
<211> LENGTH: 105
<212> TYPE: PRT
<213> ORGANISM: PtrCesA1

<400> SEQUENCE: 8

Tyr Gly Pro Gln Ser Leu Pro Thr Leu Pro Ser Pro Ser Ser Ser
1               5                   10                  15

Ser Cys Cys Cys Cys Gly Pro Lys Lys Pro Lys Lys Asp Leu Glu Glu
                20                  25                  30

Phe Lys Arg Asp Ala Arg Arg Asp Asp Leu Asn Ala Ala Ile Phe Asn
            35                  40                  45

Leu Lys Glu Ile Glu Ser Tyr Asp Asp Tyr Glu Arg Ser Leu Leu Ile
    50                  55                  60

Ser Gln Met Ser Phe Glu Lys Thr Phe Gly Met Ser Val Phe Ile
65                  70                  75                  80

Glu Ser Thr Leu Met Glu Asn Gly Gly Leu Ala Glu Ser Ala Asn Pro
                85                  90                  95

Ala Thr Met Ile Asn Glu Ala Ile His
            100                 105

<210> SEQ ID NO 9
<211> LENGTH: 105
<212> TYPE: PRT
<213> ORGANISM: PtrCesA1

<400> SEQUENCE: 9

Tyr Gly Pro Gln Ser Leu Pro Thr Leu Pro Ser Pro Ser Ser Ser
1               5                   10                  15

Ser Cys Cys Cys Cys Gly Pro Lys Lys Pro Lys Lys Asp Leu Glu Glu
                20                  25                  30

Phe Lys Arg Asp Ala Arg Arg Asp Asp Leu Asn Ala Ala Ile Phe Asn
            35                  40                  45

Leu Lys Glu Ile Glu Ser Tyr Asp Asp Tyr Glu Arg Ser Leu Leu Ile
    50                  55                  60

Ser Gln Met Ser Phe Glu Lys Thr Phe Gly Met Ser Val Phe Ile
65                  70                  75                  80

Glu Ser Thr Leu Met Glu Asn Gly Gly Leu Ala Glu Ser Ala Asn Pro
                85                  90                  95

Ala Thr Met Ile Asn Glu Ala Ile His

<210> SEQ ID NO 10
<211> LENGTH: 105
<212> TYPE: PRT
<213> ORGANISM: PtrCesA1

<400> SEQUENCE: 10

Tyr Gly Pro Gln Ser Leu Pro Thr Leu Pro Ser Pro Ser Ser Ser
1               5                   10                  15

Ser Cys Cys Cys Cys Gly Pro Lys Lys Pro Lys Lys Asp Leu Glu Glu
            20                  25                  30

Phe Lys Arg Asp Ala Arg Arg Asp Leu Asn Ala Ala Ile Phe Asn
        35                  40                  45

Leu Lys Glu Ile Glu Ser Tyr Asp Asp Tyr Glu Arg Ser Leu Leu Ile
    50                  55                  60

Ser Gln Met Ser Phe Glu Lys Thr Phe Gly Met Ser Ser Val Phe Ile
65                  70                  75                  80

Glu Ser Thr Leu Met Glu Asn Gly Gly Leu Ala Glu Ser Ala Asn Pro
                85                  90                  95

Ala Thr Met Ile Asn Glu Ala Ile His
                100                 105

<210> SEQ ID NO 11
<211> LENGTH: 105
<212> TYPE: PRT
<213> ORGANISM: PtrCesA1

<400> SEQUENCE: 11

Tyr Gly Pro Pro Ser Met Pro Ser Phe Pro Lys Ser Ser Ser Ser Ser
1               5                   10                  15

Cys Ser Cys Cys Cys Pro Gly Lys Lys Glu Pro Lys Asp Pro Ser Glu
            20                  25                  30

Leu Tyr Arg Asp Ala Lys Arg Glu Glu Leu Asp Ala Ala Ile Phe Asn
        35                  40                  45

Leu Arg Glu Ile Asp Asn Tyr Asp Glu Tyr Glu Arg Ser Met Leu Ile
    50                  55                  60

Ser Gln Thr Ser Phe Glu Lys Thr Phe Gly Leu Ser Ser Val Phe Ile
65                  70                  75                  80

Glu Ser Thr Leu Met Glu Asn Gly Gly Val Ala Glu Ser Ala Asn Pro
                85                  90                  95

Ser Thr Leu Ile Lys Glu Ala Ile His
                100                 105

<210> SEQ ID NO 12
<211> LENGTH: 105
<212> TYPE: PRT
<213> ORGANISM: PtrCesA1

<400> SEQUENCE: 12

Tyr Gly Pro Pro Ser Met Pro Ser Phe Pro Lys Ser Ser Ser Ser Ser
1               5                   10                  15

Cys Ser Cys Cys Cys Pro Gly Lys Lys Glu Pro Lys Glu Pro Thr Glu
            20                  25                  30

Leu Tyr Arg Asp Ala Lys Arg Glu Glu Leu Asp Ala Ala Ile Phe Asn
        35                  40                  45

Leu Arg Glu Ile Asp Asn Tyr Asp Glu Tyr Glu Arg Ser Met Leu Ile
    50                  55                  60

```
Ser Gln Thr Ser Phe Glu Lys Thr Phe Gly Leu Ser Ser Val Phe Ile
 65                  70                  75                  80

Glu Ser Thr Leu Met Glu Asn Gly Gly Val Ala Glu Ser Ala Asn Pro
             85                  90                  95

Ser Thr Leu Ile Lys Glu Ala Ile His
            100                 105

<210> SEQ ID NO 13
<211> LENGTH: 102
<212> TYPE: PRT
<213> ORGANISM: PtrCesA1

<400> SEQUENCE: 13

Tyr Ser Pro Pro Ser Met Pro Pro Leu Pro Lys Ser Ser Ser Cys Cys
  1               5                  10                  15

Cys Phe Pro Ser Lys Lys Pro Ala Lys Asp Val Ser Glu Leu Tyr Lys
             20                  25                  30

Asp Ala Lys Arg Glu Glu Leu Asp Ala Ala Ile Phe Asn Leu Arg Glu
         35                  40                  45

Ile Glu Asn Tyr Asp Glu Tyr Glu Arg Ser Met Leu Ile Ser Gln Leu
 50                  55                  60

Ser Phe Glu Lys Thr Phe Gly Leu Ser Thr Val Phe Ile Glu Ser Thr
 65                  70                  75                  80

Leu Met Glu Asn Gly Gly Val Ser Glu Ser Ala Asp Pro Ser Met Leu
             85                  90                  95

Ile Lys Glu Ala Ile His
            100

<210> SEQ ID NO 14
<211> LENGTH: 106
<212> TYPE: PRT
<213> ORGANISM: PtrCesA1

<400> SEQUENCE: 14

Tyr Gly Pro Pro Ser Leu Pro Ala Leu Pro Lys Ser Ser Val Cys Ser
  1               5                  10                  15

Trp Cys Cys Cys Cys Pro Lys Lys Lys Ala Glu Lys Ser Glu Lys
             20                  25                  30

Glu Met His Arg Asp Ser Arg Arg Glu Asp Leu Glu Ser Ala Ile Phe
         35                  40                  45

Asn Leu Arg Glu Ile Asp Asn Tyr Asp Glu Tyr Glu Arg Ser Met Leu
 50                  55                  60

Ile Ser Gln Met Ser Phe Glu Lys Ser Phe Gly Leu Ser Ser Val Phe
 65                  70                  75                  80

Ile Glu Ser Thr Leu Met Glu Asn Gly Gly Val Pro Glu Ser Ala Asn
             85                  90                  95

Pro Ser Thr Leu Ile Lys Glu Ala Ile His
            100                 105

<210> SEQ ID NO 15
<211> LENGTH: 108
<212> TYPE: PRT
<213> ORGANISM: PtrCesA1

<400> SEQUENCE: 15

Tyr Gly Pro Pro Ser Met Pro Ser Leu Arg Lys Arg Lys Asp Ser Ser
  1               5                  10                  15

Ser Cys Phe Ser Cys Cys Cys Pro Ser Lys Lys Lys Pro Ala Gln Asp
             20                  25                  30
```

Pro Ala Glu Val Tyr Arg Asp Ala Lys Arg Glu Asp Leu Asn Ala Ala
            35                  40                  45

Ile Phe Asn Leu Thr Glu Ile Asp Asn Tyr Asp Glu His Glu Arg Ser
        50                  55                  60

Met Leu Ile Ser Gln Leu Ser Phe Glu Lys Thr Phe Gly Leu Ser Ser
 65                  70                  75                  80

Val Phe Ile Glu Ser Thr Leu Met Glu Asn Gly Gly Val Pro Glu Ser
                85                  90                  95

Ala Asn Ser Pro Thr Leu Ile Lys Glu Ala Ile His
            100                 105

<210> SEQ ID NO 16
<211> LENGTH: 105
<212> TYPE: PRT
<213> ORGANISM: PtrCesA1

<400> SEQUENCE: 16

Tyr Ser Pro Pro Ser Lys Pro Arg Ile Leu Pro Gln Ser Ser Ser Ser
 1               5                  10                  15

Ser Cys Cys Cys Leu Thr Lys Lys Lys Gln Pro Gln Asp Pro Ser Glu
            20                  25                  30

Ile Tyr Lys Asp Ala Lys Arg Glu Glu Leu Asp Ala Ala Ile Phe Asn
        35                  40                  45

Leu Gly Asp Leu Asp Asn Tyr Asp Glu Tyr Arg Ser Met Leu Ile
 50                  55                  60

Ser Gln Thr Ser Phe Glu Lys Thr Phe Gly Leu Ser Thr Val Phe Ile
 65                  70                  75                  80

Glu Ser Thr Leu Met Glu Asn Gly Gly Val Pro Asp Ser Val Asn Pro
                85                  90                  95

Ser Thr Leu Ile Lys Glu Ala Ile His
            100                 105

<210> SEQ ID NO 17
<211> LENGTH: 93
<212> TYPE: PRT
<213> ORGANISM: PtrCesA2

<400> SEQUENCE: 17

Tyr Asn Pro Pro Lys Gly Pro Lys Arg Pro Lys Met Val Ser Cys Asp
 1               5                  10                  15

Cys Cys Pro Cys Phe Gly Ser Arg Lys Lys Leu Lys His Ala Lys Ser
            20                  25                  30

Asp Val Asn Gly Glu Ala Ala Ser Leu Lys Gly Met Asp Asp Asp Lys
            35                  40                  45

Glu Val Leu Met Ser Gln Met Asn Phe Glu Lys Lys Phe Gly Gln Ser
 50                  55                  60

Ser Ile Phe Val Thr Ser Thr Leu Met Glu Glu Gly Gly Val Pro Pro
 65                  70                  75                  80

Ser Ser Ser Pro Ala Gly Met Leu Lys Glu Ala Ile His
            85                  90

<210> SEQ ID NO 18
<211> LENGTH: 93
<212> TYPE: PRT
<213> ORGANISM: PtrCesA2

<400> SEQUENCE: 18

Tyr Asn Pro Pro Lys Gly Pro Lys Arg Pro Lys Met Val Ser Cys Asp

```
                1               5                  10                  15
Cys Cys Pro Cys Phe Gly Arg Arg Lys Val Lys His Ala Met Asn
            20                  25                  30

Asp Ala Asn Gly Glu Ala Ala Gly Leu Arg Gly Met Glu Asp Asp Lys
            35                  40                  45

Glu Leu Leu Met Ser Gln Met Asn Phe Glu Lys Lys Phe Gly Gln Ser
            50                  55                  60

Ser Ile Phe Val Thr Ser Val Leu Met Glu Glu Gly Gly Val Pro Pro
65                  70                  75                  80

Ser Ser Ser Pro Ala Ser Gln Leu Lys Glu Ala Ile His
                85                  90
```

<210> SEQ ID NO 19
<211> LENGTH: 94
<212> TYPE: PRT
<213> ORGANISM: PtrCesA2

<400> SEQUENCE: 19

```
Tyr Glu Pro Pro Lys Gly Pro Lys Arg Pro Lys Met Ile Ser Cys Gly
1               5                  10                  15

Cys Cys Pro Cys Phe Gly Arg Arg Lys Asn Lys Lys Phe Ser Lys
            20                  25                  30

Asn Asp Met Asn Gly Asp Val Ala Ala Leu Gly Gly Ala Glu Gly Asp
            35                  40                  45

Lys Glu His Leu Met Phe Glu Met Asn Phe Glu Lys Thr Phe Gly Gln
            50                  55                  60

Ser Ser Ile Phe Val Thr Ser Thr Leu Met Glu Glu Gly Gly Val Pro
65                  70                  75                  80

Pro Ser Ser Ser Pro Ala Val Leu Leu Lys Glu Ala Ile His
                85                  90
```

<210> SEQ ID NO 20
<211> LENGTH: 88
<212> TYPE: PRT
<213> ORGANISM: PtrCesA2

<400> SEQUENCE: 20

```
Tyr Asp Pro Pro Lys Asp Pro Lys Arg Pro Lys Met Glu Thr Cys Asp
1               5                  10                  15

Cys Cys Pro Cys Phe Gly Arg Arg Lys Lys Lys Asn Ala Lys Thr Gly
            20                  25                  30

Ala Val Val Glu Gly Met Asp Asn Asp Lys Glu Leu Leu Met Ser
            35                  40                  45

His Met Asn Phe Glu Lys Lys Phe Gly Gln Ser Ala Ile Phe Val Thr
            50                  55                  60

Ser Thr Leu Met Glu Glu Gly Gly Val Pro Pro Ser Ser Ser Pro Ala
65                  70                  75                  80

Ala Leu Leu Lys Glu Ala Ile His
                85
```

<210> SEQ ID NO 21
<211> LENGTH: 81
<212> TYPE: PRT
<213> ORGANISM: PtrCesA2

<400> SEQUENCE: 21

```
Phe Asp Pro Pro Lys Ala Ser Lys Arg Gln Arg Glu Val Gln Val His
1               5                  10                  15
```

```
Ser Lys Gln Asp Glu Ser Gly Glu Asp Gly Ser Ile Lys Glu Ala Thr
         20                  25                  30

Asp Glu Asp Lys Gln Leu Leu Lys Ser His Met Asn Val Glu Asn Lys
         35                  40                  45

Phe Gly Asn Ser Thr Leu Phe Met Asn Ser Ser Leu Thr Glu Glu Gly
 50                  55                  60

Gly Val Asp Pro Ser Ser Ser Gln Glu Ala Leu Leu Lys Glu Ala Ile
 65                  70                  75                  80

His
```

<210> SEQ ID NO 22
<211> LENGTH: 127
<212> TYPE: PRT
<213> ORGANISM: PtrCesA3

<400> SEQUENCE: 22

```
Tyr Asp Pro Pro Val Ser Glu Lys Arg Pro Lys Met Thr Cys Asp Cys
 1               5                  10                  15

Trp Pro Ser Trp Cys Cys Cys Cys Phe Gly Gly Ser Arg Lys Lys Ser
         20                  25                  30

Lys Lys Lys Gly Gln Arg Ser Leu Leu Gly Gly Leu Tyr Pro Met Lys
         35                  40                  45

Lys Lys Met Met Gly Lys Lys Tyr Thr Arg Lys Ala Ser Ala Pro Val
 50                  55                  60

Phe Asp Leu Glu Glu Ile Glu Glu Gly Leu Glu Gly Tyr Glu Glu Leu
 65                  70                  75                  80

Glu Lys Ser Ser Leu Met Ser Gln Lys Ser Phe Glu Lys Arg Phe Gly
         85                  90                  95

Gln Ser Pro Val Phe Ile Ala Ser Thr Leu Met Glu Asn Gly Gly Val
        100                 105                 110

Pro Glu Gly Thr Asn Ser Gln Ser His Ile Lys Glu Ala Ile His
        115                 120                 125
```

<210> SEQ ID NO 23
<211> LENGTH: 127
<212> TYPE: PRT
<213> ORGANISM: PtrCesA3

<400> SEQUENCE: 23

```
Tyr Asp Pro Pro Val Ser Glu Lys Arg Pro Lys Met Thr Cys Asp Cys
 1               5                  10                  15

Trp Pro Ser Trp Cys Cys Cys Cys Phe Gly Gly Ser Arg Lys Lys Ser
         20                  25                  30

Lys Lys Lys Gly Gln Arg Ser Leu Leu Gly Gly Leu Tyr Pro Met Lys
         35                  40                  45

Lys Lys Met Met Gly Lys Lys Tyr Thr Arg Lys Ala Ser Ala Pro Val
 50                  55                  60

Phe Asp Leu Glu Glu Ile Glu Glu Gly Leu Glu Gly Tyr Glu Glu Leu
 65                  70                  75                  80

Glu Lys Ser Ser Leu Met Ser Gln Lys Ser Leu Glu Lys Arg Phe Gly
         85                  90                  95

Gln Ser Pro Val Phe Ile Ala Ser Thr Leu Met Glu Asn Gly Gly Val
        100                 105                 110

Pro Glu Gly Thr Asn Ser Gln Ser His Ile Lys Glu Ala Ile His
        115                 120                 125
```

<210> SEQ ID NO 24

```
<211> LENGTH: 129
<212> TYPE: PRT
<213> ORGANISM: PtrCesA3

<400> SEQUENCE: 24

Tyr Asp Pro Pro Val Ser Glu Lys Arg Pro Lys Met Thr Cys Asp Cys
1               5                   10                  15

Trp Pro Ser Trp Cys Cys Cys Cys Gly Gly Ser Arg Lys Lys Ser
            20                  25                  30

Lys Lys Lys Gly Glu Lys Lys Gly Leu Leu Gly Gly Leu Leu Tyr Gly
            35                  40                  45

Lys Lys Lys Lys Met Met Gly Lys Asn Tyr Val Lys Gly Ser Ala
50                      55                      60

Pro Val Phe Asp Leu Glu Glu Ile Glu Glu Gly Leu Glu Gly Tyr Glu
65                  70                  75                  80

Glu Leu Glu Lys Ser Thr Leu Met Ser Gln Lys Asn Phe Glu Lys Arg
                85                  90                  95

Phe Gly Gln Ser Pro Val Phe Ile Ala Ser Thr Leu Met Glu Asn Gly
                100                 105                 110

Gly Leu Pro Glu Gly Thr Asn Ser Thr Ser Leu Ile Lys Glu Ala Ile
            115                 120                 125

His

<210> SEQ ID NO 25
<211> LENGTH: 129
<212> TYPE: PRT
<213> ORGANISM: PtrCesA3

<400> SEQUENCE: 25

Tyr Asp Pro Pro Val Ser Glu Lys Arg Pro Lys Met Thr Cys Asp Cys
1               5                   10                  15

Trp Pro Lys Trp Cys Cys Phe Cys Cys Gly Ser Arg Lys Thr Lys Ser
            20                  25                  30

Lys Lys Lys Ser Gly Thr Asn Gly Arg Ser Leu Phe Ser Arg Leu Tyr
            35                  40                  45

Lys Lys Lys Lys Met Gly Gly Lys Asp Tyr Val Arg Lys Gly Ser Gly
50                      55                      60

Ser Met Phe Asp Leu Glu Glu Ile Glu Gln Gly Leu Glu Gly Tyr Glu
65                  70                  75                  80

Glu Leu Glu Lys Ser Ser Leu Met Ser Gln Lys Ser Phe Glu Lys Arg
                85                  90                  95

Phe Gly Gln Ser Pro Val Phe Ile Ala Ser Thr Leu Met Glu Asn Gly
                100                 105                 110

Gly Leu Pro Glu Gly Thr Asn Thr Gln Ser Leu Val Lys Glu Ala Ile
            115                 120                 125

His

<210> SEQ ID NO 26
<211> LENGTH: 139
<212> TYPE: PRT
<213> ORGANISM: PtrCesA3

<400> SEQUENCE: 26

Tyr Glu Pro Pro Val Ser Glu Lys Arg Lys Lys Met Thr Cys Asp Cys
1               5                   10                  15

Trp Pro Ser Trp Ile Cys Cys Cys Cys Gly Gly Gly Asn Arg Asn His
            20                  25                  30
```

```
Lys Ser Asp Ser Ser Lys Lys Ser Gly Ile Lys Ser Leu Phe Ser
        35              40              45

Lys Leu Lys Lys Lys Thr Lys Lys Ser Asp Asp Lys Thr Met Ser
    50              55              60

Ser Tyr Ser Arg Lys Arg Ser Ser Thr Glu Ala Ile Phe Asp Leu Glu
65              70              75                          80

Asp Ile Glu Glu Gly Leu Glu Gly Tyr Asp Glu Leu Glu Lys Ser Ser
                85              90                      95

Leu Met Ser Gln Lys Asn Phe Glu Lys Arg Phe Gly Met Ser Pro Val
            100             105             110

Phe Ile Ala Ser Thr Leu Met Glu Asn Gly Gly Leu Pro Glu Ala Thr
            115             120             125

Asn Thr Ser Ser Leu Ile Lys Glu Ala Ile His
        130             135
```

<210> SEQ ID NO 27
<211> LENGTH: 155
<212> TYPE: PRT
<213> ORGANISM: PtrCesA3

<400> SEQUENCE: 27

```
Tyr Asp Pro Pro Arg Pro Glu Lys Arg Pro Lys Met Thr Cys Asp Cys
1               5                   10                  15

Trp Pro Ser Trp Cys Cys Cys Cys Cys Phe Gly Gly Gly Lys Arg
            20              25              30

Gly Lys Ser His Lys Asn Lys Lys Gly Gly Gly Gly Glu Gly Gly
            35              40              45

Gly Leu Asp Glu Pro Arg Arg Gly Leu Leu Gly Phe Tyr Lys Lys Arg
    50              55              60

Ser Lys Asp Lys Leu Gly Gly Gly Ala Ala Ser Leu Ala Gly Gly
65              70              75              80

Lys Lys Gly Tyr Arg Lys His Gln Arg Gly Phe Glu Leu Glu Glu Ile
            85              90              95

Glu Glu Gly Leu Glu Gly Tyr Asp Glu Leu Glu Arg Ser Ser Leu Met
            100             105             110

Ser Gln Lys Ser Phe Glu Lys Arg Phe Gly Gln Ser Pro Val Phe Ile
            115             120             125

Ala Ser Thr Leu Val Glu Asp Gly Gly Leu Pro Gln Gly Ala Ala Ala
            130             135             140

Asp Pro Ala Ala Leu Ile Lys Glu Ala Ile His
145             150             155
```

METHODS FOR ENHANCING EXPRESSION OF SECONDARY CELL WALL CELLULOSE SYNTHASES IN PLANTS

CROSS-REFERENCE TO RELATED APPLICATIONS

This application is a national stage filing under 35 U.S.C. 371 of International Application No. PCT/US2006/030316, filed on Aug. 3, 2006, which claims priority to U.S. provisional application 60/705,033, filed on Aug. 3, 2005, each of which is incorporated herein by reference in its entirety.

STATEMENT REGARDING FEDERALLY SPONSORED RESEARCH

This invention was made with United States government support from the National Science Foundation grant number IBN-0236492. The United States government has certain rights in this invention.

INTRODUCTION

Cellulose is of great commercial importance in the food, textile, paper and pulp, forest and chemical industries. Numerous genes encoding cellulose synthases have been cloned from a variety of plant species. Certain cellulose synthases are associated with primary cell wall production and are referred to as primary cell wall cellulose synthases, whereas others contribute to secondary cell wall production and are referred to as secondary cell wall cellulose synthases. There is a need in the art to obtain plants capable of growing at increased rates and producing cellulose in higher amounts. However, very little is known about cellular factors controlling these traits.

SUMMARY

Described herein is the inventor's discovery that introducing polynucleotides encoding three distinct secondary cell wall cellulose synthases into a plant yields a plant with enhanced growth. Plants transformed with polynucleotides encoding three secondary cell wall cellulose synthases were found to produce normal flowers but no seeds.

Accordingly, the invention provides methods of enhancing expression of secondary cell wall cellulose synthases in a plant comprising introducing into the plant a first polynucleotide encoding a first secondary cell wall cellulose synthase, a second polynucleotide encoding a second secondary cell wall cellulose synthase, and a third polynucleotide encoding a third secondary cell wall cellulose synthase. The plant may exhibit increased growth or reduced seed production when compared to a control plant. The invention also provides plants produced by the methods described herein.

In another aspect, a plant comprising at least three exogenous polynucleotides encoding secondary cell wall cellulose synthases is provided.

BRIEF DESCRIPTION OF THE FIGURES

FIG. 2 presents sequence alignment of secondary cell wall cellulose sequences related to PtrCesA1 (FIG. 2A), PtrCesA2 (FIG. 2B), and PtrCesA3 (FIG. 2C).

FIG. 5 is a photograph showing an overhead view of tobacco plants expressing introduced PtrCesA1 polynucleotides, PtrCesA1 and PtrCesA2 polynucleotides or PtrCesA1, PtrCesA2 and PtrCesA3 polynucleotides.

DETAILED DESCRIPTION OF SEVERAL EMBODIMENTS

In one embodiment, the invention provides methods of enhancing secondary cell wall cellulose synthases in a plant. In another embodiment, the invention provides methods of making transgenic plants capable of expressing secondary cell wall cellulose synthases. As used herein, a "secondary cell wall cellulose synthase" is a polypeptide that synthesizes cellulose, and is predominantly or exclusively localized in plant tissue or cells where secondary cell walls are formed. As used herein, "predominantly localized" means that in a plant comprising cells or tissue forming secondary cell walls, at least 80% of the total of a selected secondary cell wall cellulose synthase in the plant is found in cells or tissue forming secondary cell walls. Examples of tissues which form secondary cell walls are tissues that develop xylem and phloem fibers; however, secondary cell walls may be formed in other tissues. Examples of secondary cell wall cellulose synthases include those from *Populus tremuloides* (also referred to herein as aspen): PtrCesA1 (SEQ ID NO:2), PtrCesA2 (SEQ ID NO:4), and PtrCesA3 (SEQ ID NO:6); and those from *Arabidopsis thaliana* AtCesA4 (GenBank Accession No: AF458083), AtCesA7 (GenBank Accession No: AF088917) and AtCesA8 (GenBank Accession No: AF267742). Examples of polynucleotides encoding secondary cell wall cellulose synthases include those from *Populus tremuloides*, (also referred to herein as aspen): PtrCesA1 (SEQ ID NO:1), PtrCesA2 (SEQ ID NO:3), and PtrCesA3 (SEQ ID NO:5).

Figure 1:
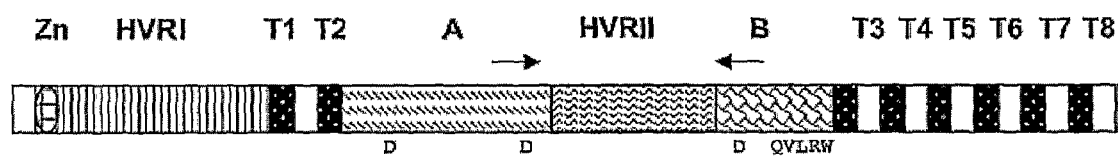
FIG. 1 is a diagrammatic representation of a PtrCesA polypeptide.

A diagrammatic representation showing the structure of a representative secondary cell wall cellulose synthase protein (e.g., PtrCesA) is shown in FIG. 1. Domains are indicated in FIG. 1 as follows: Zn represents the zinc-binding domain; HVR I represents the N-terminal hypervariable region; the numbers 1 to 8 represent the transmembrane domains; the subdomains identified by A and B are highly conserved (70-90%) parts of catalytic domains in relation to other CesA proteins; HVR II represents the central hypervariable region. Conserved D, D, D, and QVLRW (SEQ ID NO:7) motifs are also shown (Joshi et al., 2004: New Phytologist 164:53-61, which is incorporated herein by reference).

Secondary cell wall cellulose synthases useful in the invention may be identified based on the identity of consensus sequences within the HVRII. The HVRII of each of PtrCesA1, PtrCesA2 and PtrCesA3 shares common sequences with secondary cellulose synthases from other species. Alignment of the HVRII regions from PtrCesA1, PtrCesA2 and PtrCesA3 showing conserved regions are depicted in FIG. 2A-2C, respectively. Consensus amino acids within the HVRII, that is, amino acids found to show identity in at least 80% of the aligned sequences, are underlined. GenBank accession numbers and SEQ ID NO for each of the compared sequences are provided in FIG. 2. Immediately following the GenBank accession numbers in brackets is an abbreviation indicating the plant of origin. The abbreviations are as follows: At=*Arabidopsis thaliana* (L.) Heynh.; Gh=*Gossypium hirsutum* L.; Gm, *Glycine max* (L.) Merill; Mc=*Mesotaenium caldariorum* (Lagerh.) Hansg.; Na=*Nicotiana alata* Link &

Otto; Mt=*Medicago truncatula* Gaertn.; Nt, *Nicotiana tabacum* L.; Os=*Oryza sativa* L.; Pc=*Populus canescens* (Ait.) Sm.; Ze=*Zinnia elegans* Jacq.; and Zm=*Zea mays* L. SEQ ID NO:8-16 show homology to PtrCesA1. SEQ ID NO:17-21 show homology to PtrCesA2. SEQ ID NO:22-27 show homology to PtrCesA3.

Figure 3:
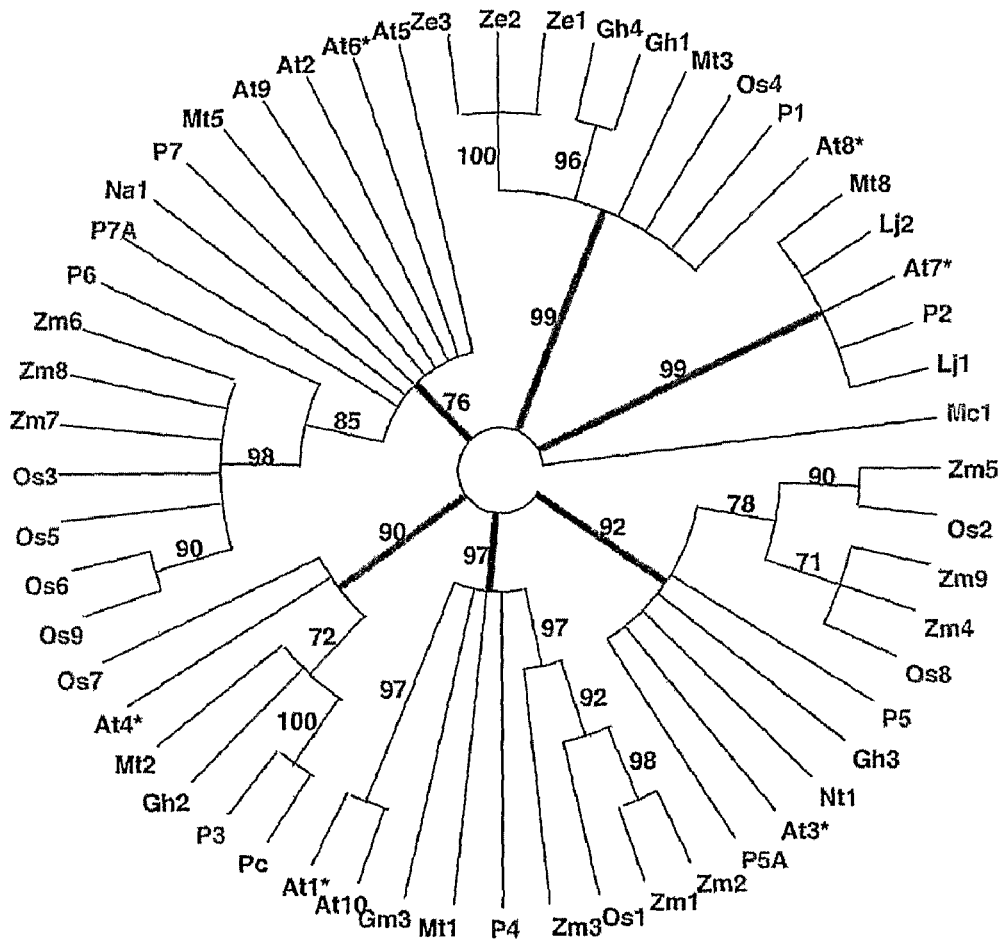
FIG. 3 depicts the phylogenetic relationship of CesA members.

A phylogenetic tree showing the relationship between primary and secondary cell wall cellulose synthases is presented in FIG. 3. FIG. 3 depicts a circular representation of a phylogenetic tree made using the PAUP program based on 56 CesA HVRII regions from plants. Bootstrap analysis was done with 1000 replicates and bootstrap values of above 70 were considered for the development of rooted tree using green algal CesA from *Mesotaenium caldarioum* (Mc) HVRII as an outgroup (GenBank Accession number AF525360). HVRII domains from all CesA proteins were downloaded from the Stanford site and were renamed by just dropping off their CesA extension in each case for simplicity of figure. The following GenBank accession numbers for aspen (underlined) or some CesA genes that are currently missing in the protein collection at the Stanford site were used to deduce the polypeptide sequences included in this figure: P1=PtrCesA1, AF072131; P2=PtrCesA2, AY095297; P3=PtrCesA3, AF527387; P4=PtrCesA4, AY162181; P5=PtrCesA 5, AY055724; P5A=PtrCesA 5-like AY330165; P6=PtrCesA6, AY196961; P7=PtrCesA 7, AY162180; P7A=PtrCesA7-like AY330166; Nt1=NtCesA1, AF233892; Mc1=McCesA1, AF525360.

As used herein, "PtrCesA1-like secondary cell wall cellulose synthase" is a polypeptide sharing homology with the HVRII of PtrCesA1. See e.g., FIG. 2A. As can be seen in FIG. 2A and FIG. 3, PtrCesA1-like secondary cell wall cellulose synthases include polypeptides from *Arabidopsis thaliana* (L.) Heynh.; *Gossypium hirsutum* L.; *Zinnia elegans* Jacq.; *Oryza sativa* L.; *Populus canescens* (Ait.) Sm.; and *Medicago truncatula* Gaertn. As used herein, "PtrCesA2-like secondary cell wall cellulose synthase" is a polypeptide sharing homology with the HVRII of PtrCesA2. See e.g., FIG. 2B. As can be seen in FIG. 2B and FIG. 3, PtrCesA2-like secondary cell wall cellulose synthases include polypeptides from *Arabidopsis thaliana* (L.) Heynh; *Lotus corniculatus* and *Medicago truncatula*. As used herein, "PtrCesA3-like secondary cell wall cellulose synthase" is a polypeptide sharing homology with the HVRII of PtrCesA3. See e.g., FIG. 2C. As can be seen in FIG. 2C and FIG. 3, PtrCesA3-like secondary cell wall cellulose synthases include polypeptides from *Arabidopsis thaliana* (L.) Heynh.; *Medicago truncatula; Oryza sativa* L.; *Populus canescens* (Ait.) Sm.; and *Gossypium hirsutum* L. Each of these secondary cell wall cellulose synthases would be expected to be useful in the present methods.

It is envisaged that methods of the invention encompass the introduction into a plant of polynucleotides encoding a PtrCesA1-like secondary cell wall cellulose synthase, a PtrCesA2-like secondary cell wall cellulose synthase and a PtrCesA3-like secondary cell wall cellulose synthase. It is envisaged that a plant produced by the introduction of polynucleotides encoding a PtrCesA1-like secondary cell wall cellulose synthase, a PtrCesA2-like secondary cell wall cellulose synthase and a PtrCesA3-like secondary cell wall cellulose synthase exhibits characteristics including, but not limited to, increased branching, for example, a bifurcated stem, enhanced growth or reduced seed production relative to a control plant. Enhanced or increased growth includes, but is not limited to, increased height, increased girth, increased leaf size, increased rate of growth or increased leaf, stem or branch number.

As used herein, a "control plant" is a plant that is substantially equivalent to a test plant in all parameters with the exception of the test parameters. For example, when referring to a plant into which polynucleotides encoding three distinct secondary cell wall cellulose synthases have been introduced, a control plant is an equivalent plant into which polynucleotides encoding zero, one, or two distinct secondary cell wall cellulose synthases have been introduced. For example, when referring to a plant encoding two distinct secondary cell wall cellulose synthases, a "control plant" is an equivalent plant into which polynucleotides encoding zero or one secondary cell wall cellulose synthases have been introduced. The control plant may be clonally related to the test plant.

Methods of enhancing expression of secondary cell wall cellulose synthases encompass introducing polynucleotides encoding secondary cell wall cellulose synthases into a plant. As used herein, "introducing into a plant" is defined to mean the delivery of a polynucleotide into a plant, plant tissue or plant cell using any suitable polynucleotide delivery method. Methods suitable for introducing polynucleotides into plants useful in the practice of the present invention include, but are not limited to, microparticle bombardment, direct DNA uptake, whisker-mediated transformation, electroporation, sonication, microinjection and plant virus-mediated and *Agrobacterium*-mediated gene transfer to the plant. Any suitable *Agrobacterium* strain, vector or vector system for transforming the plant may be employed according to the present invention. In some embodiments, a plant may be regenerated or grown from the plant tissue or plant cell. Methods for regenerating or growing a plant from a plant cell or plant tissue are known in the art.

Suitably, the polynucleotide to be introduced into the plant is placed under the control of a promoter sequence. Promoter sequences are known in the art and may be operatively connected to the polynucleotide to be introduced into the plant. "Operatively connected," as used herein and in the art, refers to a linkage of polynucleotide elements in a functional relationship. A nucleic acid is "operatively linked" or "operatively connected" when it is placed into a functional relationship with another nucleic acid sequence. For instance, a promoter is operatively linked to a coding sequence if it affects the transcription of the coding sequence.

Promoters useful in the practice of the present invention include, but are not limited to, constitutive, inducible, temporally-regulated, developmentally regulated, chemically regulated, tissue-preferred and tissue-specific promoters. Other promoters may be utilized so long as the selected promoter is capable of causing sufficient expression in a plant resulting in the production of an effective amount of the secondary cell wall cellulose synthase to produce the phenotypes described herein. A suitable constitutive promoter known in the art is the 35S promoter of the cauliflower mosaic virus. Another suitable promoter is a secondary cell wall cellulose synthase promoter, which is natively associated with a polynucleotide encoding a secondary cell wall cellulose synthase, such as the *Populus tremuloides* CesA1 (PtrCesA1) promoter. The PtrCesA1 promoter directs expression of the polynucleotide to the xylem and phloem fibers. In one embodiment, plants transformed with three polynucleotides encoding secondary cell wall cellulose synthases operatively linked to a secondary cell wall cellulose synthase promoter have bifurcated stems.

Figure 4A:
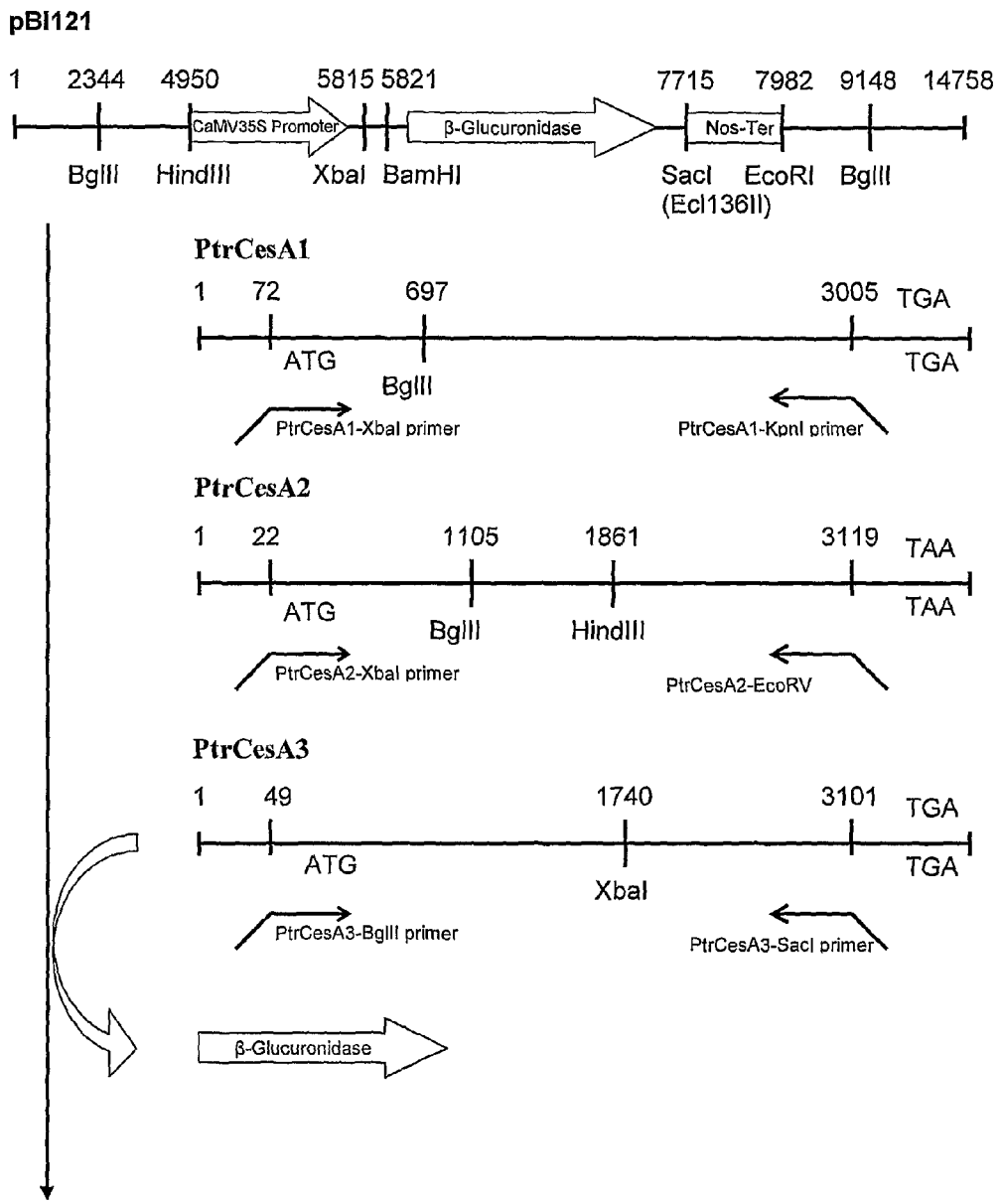
FIG. 4 depicts a representative cloning strategy that may be used for preparation of PtrCesA overexpression constructs (FIG. 4A) and the resulting constructs containing PtrCesA1, PtrCesA2 and PtrCesA3 (FIG. 4B).

In one embodiment, the polynucleotides encoding the secondary cell wall cellulose synthases are included in an expression cassette. As used herein, an "expression cassette" is a polynucleotide comprising one or more coding regions that are under the control of one or more promoters. In some embodiments, the expression cassette may further comprise one or more transcription-termination sequences. In another embodiment, the expression cassette may be contained within a plasmid vector such as the pBI121 plasmid depicted in FIG. 4A.

Suitably, one, two or three distinct secondary cell wall cellulose synthases may be introduced into a plant. For example, a plant may be transformed with a polynucleotide encoding PtrCesA1 or a PtrCesA1-like secondary cell wall cellulose synthase; a polynucleotide encoding PtrCesA2 or a PtrCesA2-like secondary cell wall cellulose synthase; or a polynucleotide encoding PtrCesA3 or a PtrCesA3-like secondary cell wall cellulose synthase, or any combination thereof. Plants transformed with polynucleotides encoding one, two or three distinct secondary cell wall cellulose synthases may display altered growth, increased branching or reduced seed production when compared to a control plant.

In one embodiment, a plant comprising at least three exogenous polynucleotides encoding secondary cell wall cellulose synthases is provided. Plants comprising exogenous polynucleotides encoding the secondary cell wall cellulose synthases encompass plants transformed or transfected with the polynucleotides, and progeny of such plants, provided the progeny retain the exogenous polynucleotides. The exogenous secondary cell wall cellulose synthases may be in addition to those naturally occurring in the plant or may replace the naturally occurring polynucleotides. The exogenous secondary cell wall cellulose synthases may encompass additional copies of the secondary cell wall cellulose synthases natively associated with the plant.

In another embodiment, methods of the invention include introducing into a plant a polynucleotide encoding a polypeptide having a sequence with at least 95% identity to SEQ ID NO:2 (PtrCesA1), or suitably, a polynucleotide encoding a polypeptide having at least 96%, 97%, 98%, 99%, or 100% identity to SEQ ID NO:2; a polypeptide having a sequence with at least 95% identity to SEQ ID NO:4 (PtrCesA2), or suitably, a polynucleotide encoding a polypeptide having at least 96%, 97%, 98%, 99%, or 100% identity to SEQ ID NO:4; and a polypeptide having a sequence with at least 95% identity to SEQ ID NO:6 (PtrCesA3), or suitably, a polynucleotide encoding a polypeptide having at least 96%, 97%, 98%, 99%, or 100% identity to SEQ ID NO:6. Plants transformed with any of the above polynucleotides encoding one, two or three distinct secondary cell wall cellulose synthases may display increased growth, increased branching, or reduced seed production when compared to a control plant.

The plant or plant cell expressing the introduced polynucleotides is considered herein to be a "transformed" plant or plant cell, or a "transgenic" plant or plant cell.

A polynucleotide encoding a selectable or screenable marker may be suitably introduced into the plant in addition to polynucleotides encoding the secondary cell wall cellulose synthases. Marker coding sequences are polynucleotides that impart a distinct phenotype to cells expressing the marker coding sequence, and thus allow such transformed cells to be distinguished from cells that do not contain the marker. Many examples of suitable marker coding sequences are known in the art and can be employed in the practice of the invention. For example, marker genes include, but are not limited to, genes conferring resistance to antibiotics or to herbicidal compounds.

Methods of the invention may be used to introduce secondary cell wall cellulose synthases into a variety of plants. Suitable plants include, but are not limited to, woody plants, trees, and crop plants such as alfalfa, cotton, maize, rice, tobacco, pines, eucalyptus, poplar, fir, maple, oak, and acacia plants. A "woody plant" is herein defined as a perennial plant whose stem comprises woody tissue. Examples of woody plants may include trees, shrubs or vines.

Suitably, plants in which the expression of three secondary cell wall cellulose synthases is enhanced do not produce seeds naturally and grow faster than plants in which the expression of zero, one, or two secondary cell wall cellulose synthases are enhanced when compared with a control plant.

The following examples are included to demonstrate preferred embodiments of the invention. It should be appreciated by those of skill in the art that the techniques disclosed in the examples which follow, represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

The materials and methods described below are used in Examples 2 and 3.

A. Preparation of Constructs

Three binary vector constructs comprising PtrCesA1, PtrCesA2 or PtrCesA3 were prepared as follows. The pBI121 backbone was used to make these constructs, with the GUS gene replaced by a specific PtrCesA in the sense direction. In each of the three cases, a specific PtrCesA cDNA was amplified using a primer pair that incorporates the necessary unique restriction sites for cloning the specific PtrCesA in pBI121 vector, as shown in FIG. 4.

For the PtrCesA1 overexpression construct, pBI121 was digested by XbaI and Ecl136II (an isoschizomer of SacI which produces a blunt end) (Fermentas, N.Y.), resulting in an open vector with 5' end sticky and 3' end blunt. PtrCesA1 cDNA was amplified from an existing plasmid in pBluescript vector using a pair of primers with XbaI site at the 5' end and KpnI site at the 3' end in the presence of pfu enzyme. This amplified product was then digested with XbaI (the 3' end is already blunt due to amplification with pfu) and cloned in the open pBI121 vector.

For the PtrCesA2 overexpression construct, pBI121 was also digested by XbaI and Ecl136II, resulting in an open vector with 5' end sticky and 3' end blunt. PtrCesA2 cDNA was amplified using a pair of primers with XbaI site at the 5' end and EcoRV site at the 3' end and the amplified product was cloned in pCR2.1. This plasmid was then digested with XbaI (sticky) and EcoRV (blunt)(both unique) and cloned in open pBI121 vector.

For PtrCesA3 overexpression construct, pBI121 was digested with BamHI and SacI. PtrCesA3 cDNA was amplified using a pair of primers with a BglII site at the 5' end and SacI site at the 3' end and the amplified product was cloned in pCR2.1. This plasmid was then digested with BglII and SacI (both unique and sticky) and cloned in open pBI121 vector.

The correctness of each construct was confirmed by restriction digestion of each resultant plasmid with a pair of specific restriction enzymes in each case as shown above. PtrCesA1 binary construct was double digested with BglII and HindIII and the expected DNA fragments of 8 kb, 3.5 kb, 2.6 kb and 1.4 kb were obtained (FIG. 4B). Similarly PtrCesA2 binary construct was digested with BglII and HindIII and the expected fragments of 8 kb, 2.6 kb, 1.8 kb, 1.4 kb, 1.3 kb and 0.8 kb resulted (FIG. 4B). Finally, PtrCesA3 construct was digested with XbaI and SacI and resulted in three fragments of 13 kb, 1.7 kb and 1.4 kb as expected (FIG. 4B).

B. Transformation of Tobacco Plants

The strategy described in Li et al., 2003 (Proc. Natl. Acad. Sci. USA 100:4939-4944), and U.S. patent application Ser. No. 10/110,091, (both of which are incorporated herein by reference in their entireties) was used to transfer up to three cellulose synthase genes to tobacco plants. Briefly, the PtrCesA1, PtrCesA2 and PtrCesA3 constructs described in Example 1 were introduced separately into *Agrobacterium* strain C58 for co-infection of the same explant. The *Agrobacterium* strains comprising each construct were mixed and cultured in the following combinations to facilitate infection of plants with one, two, or all three PtrCesA constructs: PtrCesA1; PtrCesA2; PtrCesA3; PtrCesA1 and PtrCesA2; PtrCesA1 and PtrCesA3; PtrCesA2 and PtrCesA3; PtrCesA1, PtrCesA2 and PtrCesA3. Tobacco leaf explants were surface sterilized and infected with an overnight-grown culture of *Agrobacterium* carrying the overexpression constructs.

After about 2 days of co-cultivation of the explant with *Agrobacterium*, bacteria were killed with clarforan and ticarcillin (300 mg/l each). Explants were placed on callus induction medium containing kanamycin (50 mg/l) and claforan (300 mg/l). Tobacco calli were first grown on Kanamycin-containing rooting media for one month, acclimatized for one month in a mist chamber and then transferred to the greenhouse. Greenhouse conditions comprised a 16-hour day, 8-hour night, with a temperature of 25° C. and a humidity of at least 50%. The presence of the transgenes was confirmed by PCR, RNA and protein studies.

C. Transformation of Aspen Plants

Transformation of aspen using *Agrobacterium* will be performed using standard protocols according to, e.g., Tsai et al., 1994; Plant Cell Reports 14, 94-97; Tsai et al., 1998; Plant Physiology 117(5), 101-112; Hu et al., 1999; Nature Biotechnology 17, 808-812; or Li et al., 2003 Proc. Natl. Acad. Sci. USA 100:4939-4944 (each of which is incorporated herein by reference). After about two months on callus induction medium (with monthly subculture), healthy looking calli will be transferred to shoot induction medium and about two months later to root induction medium. Aspen plants will be transferred to the greenhouse after proper acclimatization, generally 6-8 months after the initial infection with *Agrobacterium*. The presence of the transgenes will be confirmed by PCR, RNA and protein studies.

Example 2

Aspen and Tobacco Plants Transformed with One, Two or Three Secondary Cell Wall Cellulose Synthases Under the Control of the 35S Promoter A. Tobacco Tobacco plants expressing the PtrCesA1, PtrCesA2, and PtrCesA3 polynucleotides under the control of the 35S cauliflower mosaic virus constitutive promoter grew faster and were taller than mature tobacco plants expressing zero, one or two of the introduced PtrCesA1, PtrCesA2, or PtrCesA3 polynucleotides (see FIG. 5).

B. Aspen

Aspen plants expressing all three introduced secondary cell wall cellulose synthase polynucleotides (PtrCesA1, PtrCesA2, and PtrCesA3) each under the control of the 35S cauliflower mosaic virus constitutive promoter will grow more vigorously and faster than those comprising zero, one or two of the introduced PtrCesA1, PtrCesA2, or PtrCesA3 polynucleotides. During regeneration of the plants, explants will grow faster than plants comprising only the vector, or those expressing two of the secondary cell wall cellulose synthase polynucleotides. The plants expressing introduced secondary cell wall cellulose synthases will have larger leaf sizes and faster stem growth than control plants.

Example 3

Tobacco Plants Comprising 1, 2 or 3 Secondary Cell Wall Cellulose Synthases Under the Control of the PtrCesA1 Promoter The mean heights of transgenic tobacco plants expressing zero, one, two or all three of the introduced PtrCesA1, PtrCesA2, or PtrCesA3 polynucleotides are presented in Table 2. Table 2 also shows the mean girth of plants 45 days after transfer to the greenhouse. The number of plants of each type is indicated in parenthesis. A1, A2 and A3 are used in Table 2 as an abbreviation for plants overexpressing vectors carrying PtrCesA1, 2 and 3 respectively. Control pBI121 in Table 2 represents a plant transformed with the pBI121 vector only. Measurements presented in Table 2 were taken when the plants were approximately 3-months old, at 15 days, 30 days and 45 days after being transferred to the greenhouse.

TABLE 2

Height and girth of tobacco plants 15, 30 or 45 days after transfer to the greenhouse

| | Height (cm) | | | Girth (mm) |
|---|---|---|---|---|
| | 15 days | 30 days | 45 days | 45 days |
| Control pBI121 (1) | 26 | 30 | 50 | 9.3 |
| A1 (1) | 26 | 35 | 53 | 8.9 |
| A2 (0) | — | — | — | — |
| A3 (1) | 18 | 28 | 55 | 10.8 |
| A1 + A2 (1) | 25 | 30 | 55 | 10.1 |
| A1 + A3 (3) | 22 | 30 | 53 | 11.93 |
| A2 + A3 (1) | 20 | 28 | 60 | 14.1 |
| A1 + A2 + A3 (2) | 38 | 63 | 69 | 12.15 |

Plants expressing PtrCesA1, PtrCesA2 and PtrCesA3 grew much faster than those expressing zero, one or two introduced secondary cell wall cellulose synthases. For example, 15 days after transfer to the greenhouse, plants expressing all three of the introduced secondary cell wall cellulose synthases were at least 12 cm taller than plants expressing zero, one or two introduced secondary cell wall cellulose synthases. Also, between 15 days and 30 days after transfer to the greenhouse plants expressing all three of the introduced secondary cell wall cellulose synthases grew 25 cm, compared with 4 to 10 cm of plants expressing zero, one or two introduced secondary cell wall cellulose synthases. Leaves were also larger at each time point in plants expressing all three of the introduced secondary cell wall cellulose synthases (FIG. 5A, plant C) compared with corresponding plants expressing zero, one (FIG. 5A, plant A) or two (FIG. 5A, plant B) introduced secondary cell wall cellulose synthases.

Plants expressing one, two or three of the introduced secondary cell wall cellulose synthases flowered normally. However, none of these plants, whether expressing one, two or all three of PtrCesA1, PtrCesA2 and PtrCesA3 polynucleotides, produced any seed naturally. Flowers fell off the plant before the normal seed set, and thus yielded no seed. Forced selling of the plants resulted in a few seeds being produced. In contrast, plants transformed with only vector produced seed normally.

Tobacco plants expressing all three of the introduced PtrCesA1, PtrCesA2 and PtrCesA3 polynucleotides under the control of the PtrCesA1 promoter produced a bifurcated stem (see FIG. 5B) which was not seen in plants expressing zero, one or two of the introduced PtrCesA1, PtrCesA2 and PtrCesA3 polynucleotides.

All patents and publications listed or described herein are incorporated in their entirety by reference.

All of the compositions and methods disclosed and claimed herein can be made or executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

---

What is claimed is:

1. A method for enhancing expression of secondary cell wall cellulose synthases in a plant comprising introducing into the plant a first polynucleotide encoding a polypeptide having at least 80% identity to SEQ ID NO:2 (PtrCesA1), a second polynucleotide encoding a polypeptide having at least 80% identity to SEQ ID NO:4 (PtrCesA2), and a third polynucleotide encoding a polypeptide having at least 80% identity to SEQ ID NO:6 (PtrCesA3), wherein the expression of secondary cell wall cellulose synthases is enhanced.

2. The method of claim 1, wherein the first polynucleotide encodes a polypeptide having at least 95% identity to SEQ ID NO:2 (PtrCesA1), the second polynucleotide encodes a polypeptide having at least 95% identity to SEQ ID NO:4 (PtrCesA2), and the third polynucleotide encodes a polypeptide having at least 95% identity to SEQ ID NO:6 (PtrCesA3).

3. The method of claim 1, wherein the first polynucleotide encodes a polypeptide of SEQ ID NO:2 (PtrCesA1), the second polynucleotide encodes a polypeptide of SEQ ID NO:4 (PtrCesA2), and the third polynucleotide encodes a polypeptide of SEQ ID NO:6 (PtrCesA3).

4. The method of claim 1, wherein the plant is a woody plant.

5. The method of claim 4, wherein the woody plant is a tree.

6. The method of claim 1, wherein the plant is selected from a alfalfa, cotton, maize, rice, tobacco, pine, eucalyptus, poplar, fir, maple, oak and acacia plant.

7. The method of claim 1, wherein the first, second and third polynucleotides are operatively linked to a promoter.

8. The method of claim 7, wherein the promoter is a constitutive promoter.

9. The method of claim 7, wherein the promoter is natively associated with a polynucleotide encoding a secondary cellulose synthase.

10. The method of claim 1, wherein the plant comprises a bifurcated stem.

11. The method of claim 1, wherein the plant exhibits increased growth or reduced seed production when compared to a control plant.

12. A plant produced by the method of claim 1.

13. The plant of claim 12, wherein the plant is a woody plant.

14. The plant of claim 13, wherein the plant is a tree.

15. The plant of claim 12, wherein the plant is selected from an alfalfa, cotton, maize, rice, tobacco, pine, eucalyptus, poplar, fir, maple, oak and acacia plant.

16. A plant comprising at least three exogenous polynucleotides encoding secondary cell wall cellulose synthases, wherein three exogenous polynucleotides encode a polypeptide having at least 80% identity to SEQ ID NO:2 (PtrCesA1), a polypeptide having at least 80% identity to SEQ ID NO:4 (PtrCesA2), and a polypeptide having at least 80% identity to SEQ ID NO:6 (PtrCesA3).

17. The plant of claim 16, wherein the plant is a woody plant.

* * * * *